United States Patent
Raghavan et al.

(10) Patent No.: US 10,299,738 B2
(45) Date of Patent: May 28, 2019

(54) GAME-BASED SENSORIMOTOR REHABILITATOR

(71) Applicant: New York University, New York, NY (US)

(72) Inventors: Preeti Raghavan, Brooklyn, NY (US); Vikram Kapila, West Orange, NJ (US)

(73) Assignee: NEW YORK UNIVERSITY, New York, NY (US)

( * ) Notice: Subject to any disclaimer, the term of this patent is extended or adjusted under 35 U.S.C. 154(b) by 529 days.

(21) Appl. No.: 14/942,971

(22) Filed: Nov. 16, 2015

(65) Prior Publication Data

US 2016/0067136 A1 Mar. 10, 2016

Related U.S. Application Data

(63) Continuation-in-part of application No. PCT/US2014/038124, filed on May 15, 2014.
(Continued)

(51) Int. Cl.
*A61B 5/00* (2006.01)
*A61B 5/11* (2006.01)
(Continued)

(52) U.S. Cl.
CPC ............ *A61B 5/744* (2013.01); *A61B 5/1114* (2013.01); *A61B 5/1125* (2013.01); *A61B 5/225* (2013.01); *A61B 5/486* (2013.01); *A61B 5/6806* (2013.01); *A61B 5/6823* (2013.01); *A61B 5/7455* (2013.01); *A63B 21/072* (2013.01); *A63B 22/00* (2013.01); *A63F 13/212* (2014.09); *A63F 13/218* (2014.09); *A63F 13/24* (2014.09); *A63F 13/428* (2014.09); *G06F 3/011* (2013.01); *G06F 3/014* (2013.01); *G06F 3/016* (2013.01); *G06F 3/0346* (2013.01); *G06F 19/3481* (2013.01); *G09B 19/003* (2013.01); *A61B 5/1126* (2013.01); *A61B 5/6804* (2013.01); *A61B 2505/09* (2013.01); *A61B 2562/0219* (2013.01); *A61B 2562/0257* (2013.01); *A63B 21/00061* (2013.01); *A63B 21/0602* (2013.01); *A63B 23/1209* (2013.01); *A63B 23/1245* (2013.01); *A63B 23/16* (2013.01); *A63B 24/0087* (2013.01); *A63B 71/0009* (2013.01); *A63B 71/0622* (2013.01); *A63B 2022/0092* (2013.01);
(Continued)

(58) Field of Classification Search
CPC .................................................... A61B 5/1125
USPC ......................................................... 434/247
See application file for complete search history.

(56) References Cited

U.S. PATENT DOCUMENTS

| | | | |
|---|---|---|---|
| 6,026,322 A | 2/2000 | Korenman et al. | |
| 2012/0094260 A1* | 4/2012 | Akins | G09B 19/003 434/219 |
| 2012/0157263 A1* | 6/2012 | Sivak | G06F 3/014 482/4 |

FOREIGN PATENT DOCUMENTS

| WO | WO 2007/138598 | 12/2007 |
|---|---|---|
| WO | WO 2009/050715 | 4/2009 |

OTHER PUBLICATIONS

International Search Report and Written Opinion for Application No. PCT/US2014/038124, dated Oct. 8, 2014, 8 pages.

* cited by examiner

*Primary Examiner* — Thomas Hong
(74) *Attorney, Agent, or Firm* — Foley & Lardner LLP

(57) ABSTRACT

Treatment of neurological injury through motor relearning. A game-based sensorimotor rehabilitator that enables indi-
(Continued)

viduals to interact with the functional objects using the appropriate amount of force, tilt, finger movement, and muscle activity to regain lost skill due to injury.

5 Claims, 25 Drawing Sheets

Related U.S. Application Data

(60) Provisional application No. 62/152,315, filed on Apr. 24, 2015, provisional application No. 61/824,258, filed on May 16, 2013.

(51) Int. Cl.
| | |
|---|---|
| *A61B 5/22* | (2006.01) |
| *A63B 21/072* | (2006.01) |
| *G06F 3/01* | (2006.01) |
| *G09B 19/00* | (2006.01) |
| *G06F 19/00* | (2018.01) |
| *A63F 13/428* | (2014.01) |
| *A63F 13/24* | (2014.01) |
| *A63F 13/218* | (2014.01) |
| *A63F 13/212* | (2014.01) |
| *G06F 3/0346* | (2013.01) |
| *A63B 71/00* | (2006.01) |
| *A63B 71/06* | (2006.01) |
| *A63B 21/06* | (2006.01) |
| *A63B 23/12* | (2006.01) |
| *A63B 23/16* | (2006.01) |
| *A63B 24/00* | (2006.01) |
| *A63B 22/00* | (2006.01) |
| *A63B 21/00* | (2006.01) |

(52) U.S. Cl.
CPC ............ *A63B 2022/0094* (2013.01); *A63B 2024/0096* (2013.01); *A63B 2071/065* (2013.01); *A63B 2071/0625* (2013.01); *A63B 2071/0655* (2013.01); *A63B 2071/0658* (2013.01); *A63B 2071/0661* (2013.01); *A63B 2209/10* (2013.01); *A63B 2220/10* (2013.01); *A63B 2220/40* (2013.01); *A63B 2220/51* (2013.01); *A63B 2220/52* (2013.01); *A63B 2220/54* (2013.01); *A63B 2220/58* (2013.01); *A63B 2225/02* (2013.01); *A63B 2225/20* (2013.01); *A63B 2225/50* (2013.01); *A63B 2230/60* (2013.01)

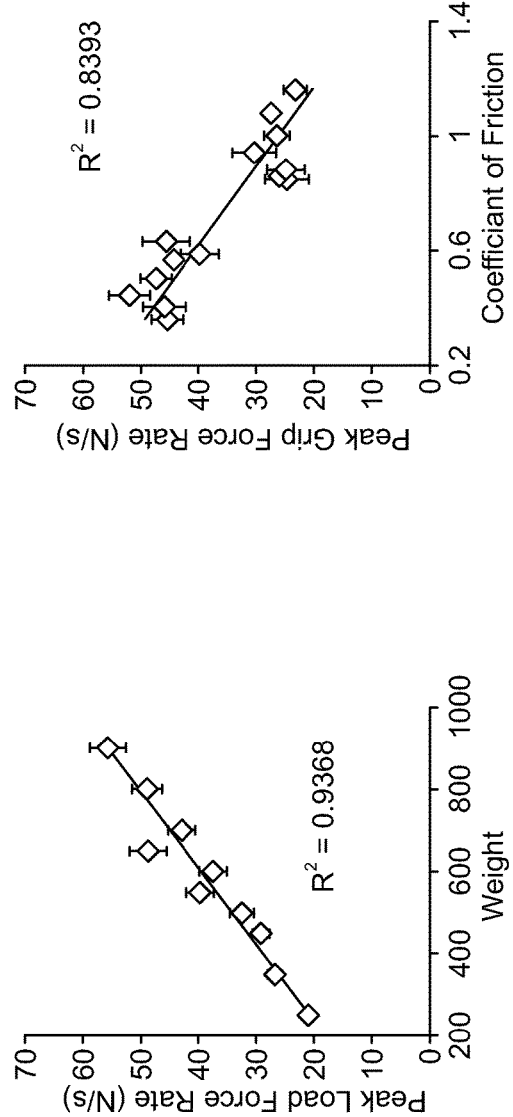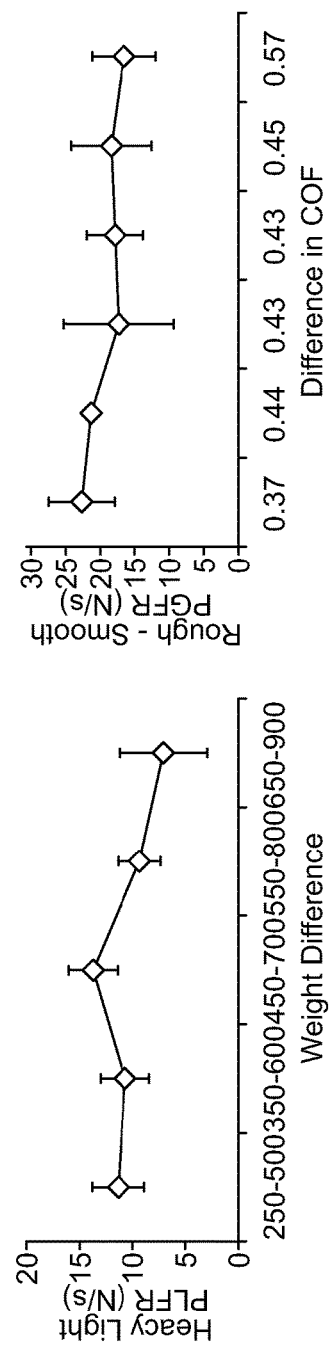
FIG. 19B
FIG. 19A
FIG. 20B
FIG. 20A

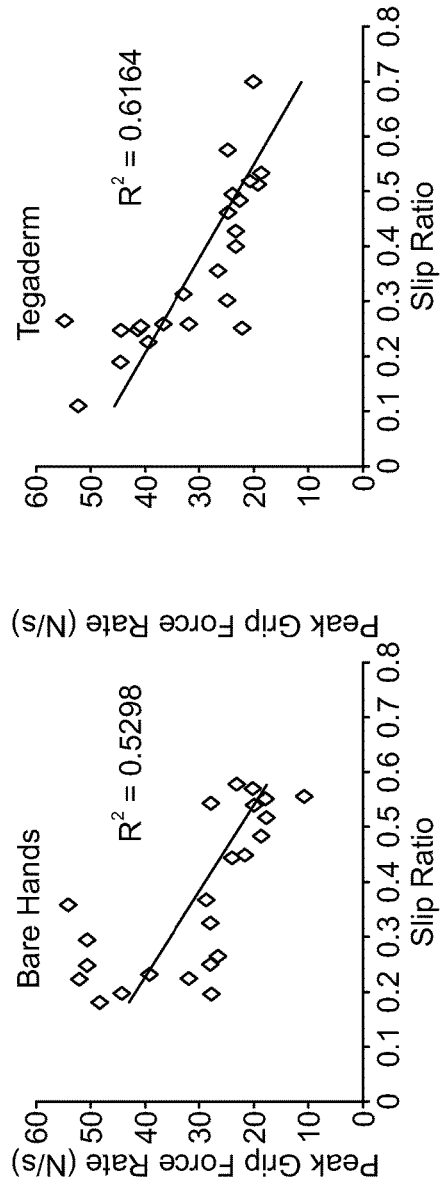
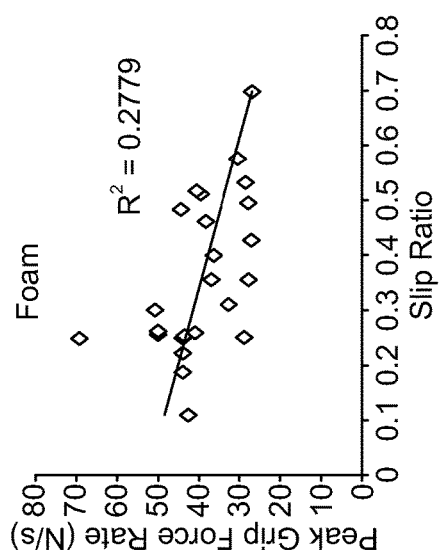
FIG. 21A
FIG. 21B
FIG. 21C

GAME-BASED SENSORIMOTOR REHABILITATOR

CROSS-REFERENCE TO RELATED APPLICATIONS

This application is a Continuation-In-Part of US Application PCT/US2014/038124, filed May 15, 2014, incorporated herein by reference in its entirety, which claims priority from Provisional Application U.S. Application 61/824,258, filed May 16, 2013, incorporated herein by reference in its entirety. This application claims priority from Provisional Application U.S. Application 62/152,315, filed Apr. 24, 2015, incorporated herein by reference in its entirety.

BACKGROUND OF THE INVENTION

Even basic tasks such as feeding ourselves, manipulating tools, and performing activities of daily living require some skill. Using specialized tools, for example by machinists such as welders, musicians, chefs and surgeons requires even more skill acquired through motor learning which requires extended practice. One main event that can impact the ability to perform these tasks is stroke.

There are over 8 million stroke survivors in the US. Majority of them do not have access to rehabilitation and have persistent hand dysfunction leading to chronic disability. Recovery of hand function after neurological injury such as stroke, cerebral palsy, multiple sclerosis, spinal cord injury etc. is extremely challenging. Recovery occurs through motor re-learning during which specific sensory-motor associations are formed to shape hand posture to match that of the object, and scale fingertip forces to the weight and texture of objects. These associations need to be fine-tuned through practice and established in long-term procedural memory to regain skill. However forming such task-specific memory requires flexible interaction with various types of objects in a systematic manner, appropriately rewarded for accuracy that can be repeated without becoming tiresome. Furthermore, it is challenging to facilitate the formation of specific sensory-motor associations because individuals tend to use compensatory strategies, such as increasing the abduction angle at the shoulder, and excessively co-activating the flexor and extensor muscles across a joint when attempting to complete the task. These compensatory strategies reinforce abnormal movements which makes it more difficult to regain skill in the long term.

Hemiparesis is the most common impairment after stroke and typically affects the upper extremity more than the lower extremity. Studies indicate that upper-extremity weakness, spasticity, and abnormal motor synergies are insufficient to explain the impairment in reaching movements after stroke (Twitchell, 1959; Wing et al., 1990; Roby-Brami et al., 1997), and suggest that additional higher-order control deficits may be present (Beer et al., 1999).

A well-characterized paradigm for the study of higher order sensorimotor integration in hand motor control is to measure subject's ability to anticipate the fingertip forces required to grasp and lift objects (Johansson, 1996). Anticipatory (feed-forward) fingertip force control ensures the generation of appropriate grip and load forces so as to avoid crushing delicate objects or dropping heavy ones, and is thought to be based on the formation of internal models of object properties in the central nervous system (Johansson and Westling, 1988; Gordon et al., 1993; Flanagan, 1999; Davidson and Wolpert, 2004). Anticipatory control of grasp is reflected in the ability to scale peak grip force rates (GFR) and peak load force rates (LFR) to the texture and weight of objects before confirmatory feedback becomes available (Johansson and Westling, 1988; Flanagan et al., 2001). Healthy subjects are able to appropriately scale peak force rates to object properties after just one or two lifts, and accurately recall those 24 hours later (Gordon et al., 1993; Flanagan et al., 2001).

Planning of precision grasp was assessed by measurement of anticipatory scaling of peak LFR and peak GFR to object weight, as the peak amplitude of these variables is scaled to the expected weight of the object before sensory feedback signaling the object's weight is available at lift-off (Johansson and Westling, 1988; Gordon et al., 1993; Flanagan et al., 2001). Scaling of the peak force rate ensures that the time to produce lifting forces does not increase linearly with object weight. Precision grasp execution was assessed by measurement of the timing and efficiency of grip-load force coordination, as these variables indicate the degree of fine motor control necessary for precision grasp (Forssberg et al., 1999). Transfer paradigms are likely to give us a better understanding of how information is exchanged between the two hemispheres and may have important implications for the development of rehabilitation strategies that incorporate practice with the non-involved hand prior to practice with the involved hand to improve grasping behavior after stroke (Raghavan et al, 2006).

The ability to predict and anticipate the mechanical demands of the environment promotes smooth and skillful motor actions. Thus, the finger forces produced to grasp and lift an object are scaled to the physical properties such as weight. Information about the relevant object properties can also be inferred from visual cues. A particularly important cue is the size of the object, which enables an estimation of the weight when the material is known. It has been frequently demonstrated that grip and load forces indeed anticipate object size (Gordon et al. 1991a, b; Cole 2008; Li et al. 2009). In addition to size, other physical object characteristics determine the grip force necessary to hold an object. Thus, friction at the finger-object contact is crucial and it has been shown that changes in the objects surface material with altering friction are precisely anticipated on the basis of the last lifting trial (Cadoret and Smith 1996; Flanagan and Johansson 2002; Johansson and Westling 1984).

Motor learning has been shown to occur over multiple time-scales. At least three underlying processes are thought to contribute to learning: (1) error-based adaptation (fast process), (2) repetition that alters movement biases depending on what is repeated (slow process), and (3) reinforcement that occurs when error is reduced successfully and leads to savings or faster re-learning on subsequent attempts. Currently available interactive platforms do not facilitate real-time interaction with kinesthetic and haptic feedback in a controlled and paced manner for rehabilitation. There is a need for systems and methods to enhance motor re-learning for restoration of hand function, especially after stroke. In particular, there is a need for a low cost commercial device that can measure grip and load forces applied by the subjects to measure dexterity. There is also a need for systems and method of statistical analysis for interpreting clinical data from such devices for the purpose of diagnosis of the extent of hand dysfunction, prognosticate improvement with specific types of therapy and to provide feedback and metrics on degree of improvement.

SUMMARY OF THE INVENTION

The foregoing summary is illustrative only and is not intended to be in any way limiting. In addition to the illustrative aspects, embodiments, and features described above, further aspects, embodiments, and features will become apparent by reference to the following drawings and the detailed description.

In one implementation, the invention includes systems and methods to help restore dexterity and functional hand use in patients with neurologic impairment from various conditions, for example, stroke, cerebral palsy, spinal cord injury, multiple sclerosis etc. The objective of this game-based physical therapy schema is to engage individuals using a biofeedback strategy to facilitate a patient's brain to develop alternate neural pathways to overcome the damage produced by the stroke. The game will provide an in-home option to encourage the patient to perform therapy more frequently to hasten their improvement and minimize the stress associated with travel to therapy centers. The concept leverages current interest in computer games on small inexpensive wireless communication devices with sophisticated biomechanical algorithms to generate clinical metrics of performance and biofeedback. Data from the biomechanical analyses will be accessible to one or more providers and be interfaced with the electronic medical record for their input and direction. The schema can also be adapted to generate training platforms for patients with other types of muscular deficits and in intact individuals.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 14A illustrates normalized muscle activity, FIG. 14B illustrates the extensor digitorum communis.

FIGS. 19A-19B show linear relationships between variables measuring grasp adaptation and object weight and texture.

FIGS. 20A-20B show similar difference in peak force rates for specified weight and texture pairs in healthy individuals.

FIGS. 21A-21C show correlation between the Slip Ratio and Peak Grip Force Rate for a series of lifts of different textured objects performed with bare hands, a thin film of Tegaderm over the fingertips, and a coating of foam over the fingers.

FIG. 26 shows the plot obtained from load forces, grip forces and corresponding load force rates for trials obtained from healthy subjects lifting objects with mass of 250 and 500 grams. FIG. 26 computes load force rates by direct differentiation after implementation of moving average filter.

FIG. 27 shows the plot obtained from load forces, grip forces and corresponding load force rates for trials obtained from healthy subjects lifting objects with mass of 250 and 500 grams. FIG. 26 computes load force rates by direct differentiation after implementation of moving average filter.

DETAILED DESCRIPTION OF THE PREFERRED EMBODIMENTS

Figure 1:
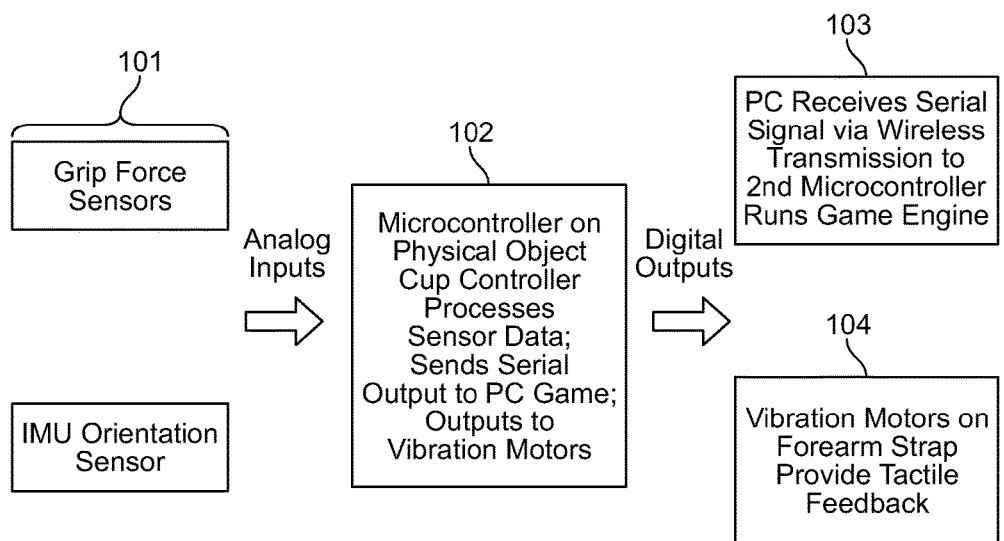
FIG. 1 Schematic of the components of the device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The description of illustrative embodiments is presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

The purpose of the present invention is to create a portable therapeutic platform to facilitate skill training/retraining anywhere, anytime using a novel game controller, such as a game-based sensorimotor rehabilitator, that serves as a virtual coach to provide skill training in both healthy and in neurologically impaired individuals using real-time tactile, kinesthetic and visual feedback. One implementation is comprised of three components: 1) the game controller, such as a cup or ball or other tool or implement, 2) a microcontroller, and 3) a computing device, such as a handheld/laptop/desktop computer running game-analysis software. In one implementation, illustrated in FIG. 1, sensor information 101 is provided from the game controller to a microcontroller 102, which may be on the game controller or separate. The microcontroller 102 determines the game controller's state, e.g. force being applied, orientation, acceleration, velocity, etc. The microcontroller 102 determines if the game controller's state is within a predetermined set of ranges for a particular application, for example tilt of the game controller in a simulation involving a cup. The microcontroller 102 provides information to a computing device 103 and to a feedback device 104.

In one aspect, an interactive gaming platform is implemented on a handheld, laptop or desktop computer systems with web access. The system may include software-based portions and a hardware-in-the-loop interface through a real object. It is anticipated that such will have wide applicability in homes, gyms, and rehabilitation centers for patients with neurologic impairment from various conditions, e.g., stroke, cerebral palsy, spinal cord injury, multiple sclerosis, etc. A successful rehabilitation outcome will restore dexterity and flexible functional hand use with wide access to facilitate tele-diagnostics and tele-treatment through easy modification of gaming parameters. Certain implementations provide systems and methods to restore adaptation, facilitate grasp efficiency and normal directional biases during repetition and enhance the rate of learning to improve hand function and quality of life post stroke.

Motor adaptation occurs when sensory information relevant to the task is extracted to form sensorimotor associations, which are used to predict accurate responses to similar actions in the future. Adaptation is the pivotal process in that it utilizes error feedback to identify the optimal movement for a task faster, which when reinforced through repetition can enhance learning for sustained changes in skill. It has been noted that patients are unable to adapt their fingertip forces and movements predictively to the expected consequences of an action with the affected hand post-stroke, perhaps because sensorimotor information from the affected side is inaccurate and/or its integration is disrupted.

However, somatosensory and visual information from each side of the body is processed bilaterally, and interlimb coordination is mediated by motor representations in the parietal and premotor areas shared by both limbs. Early in recovery after stroke, the undamaged hemisphere shows increased activation, but eventually normal sensorimotor lateralization is restored in the stroke-affected hemisphere. This suggests that redundant homologous pathways in the intact hemisphere facilitate reorganization within the affected hemisphere by mechanisms such as unmasking projections from the intact motor cortex to the cervical spinal cord, and axonal sprouting and formation of novel subcortical projections. In the chronic post-stroke period, independent finger movements of the recovered hand show a bilateral increase in regional cerebral blood flow in the dorsolateral and medial premotor areas, which are involved in motor planning. Disruption of activity in the dorsal premotor cortex of the intact hemisphere results in degraded behavior in the paretic hand. Thus, sensory information from each hand is represented bilaterally, providing redundant circuits that can be harnessed for recovery. These results suggest that actions from each hand are represented bilaterally and representations in the intact hemisphere can facilitate planning and control in the affected hand post stroke. Therefore, certain implementations utilize practice with the unaffected hand followed by practice with the affected hand to achieve adaptation of fingertip forces.

First, alternate hand training is provided to restore adaptation of fingertip forces in the affected hand. Skilled hand function requires that users grasp objects of various weights, textures, and shapes. It is believed that successful transfer of adaptation from the unaffected hand to the affected hand occurs readily when task-relevant sensory information is provided. This information may be kinesthetic, tactile or visual, and can be provided using alternative hand practice to form accurate sensorimotor associations. The understanding of how sensory modalities interact, given existing sensorimotor impairments, informs the structure of effective training protocols for adaptation.

Figures 10, 11, 12:
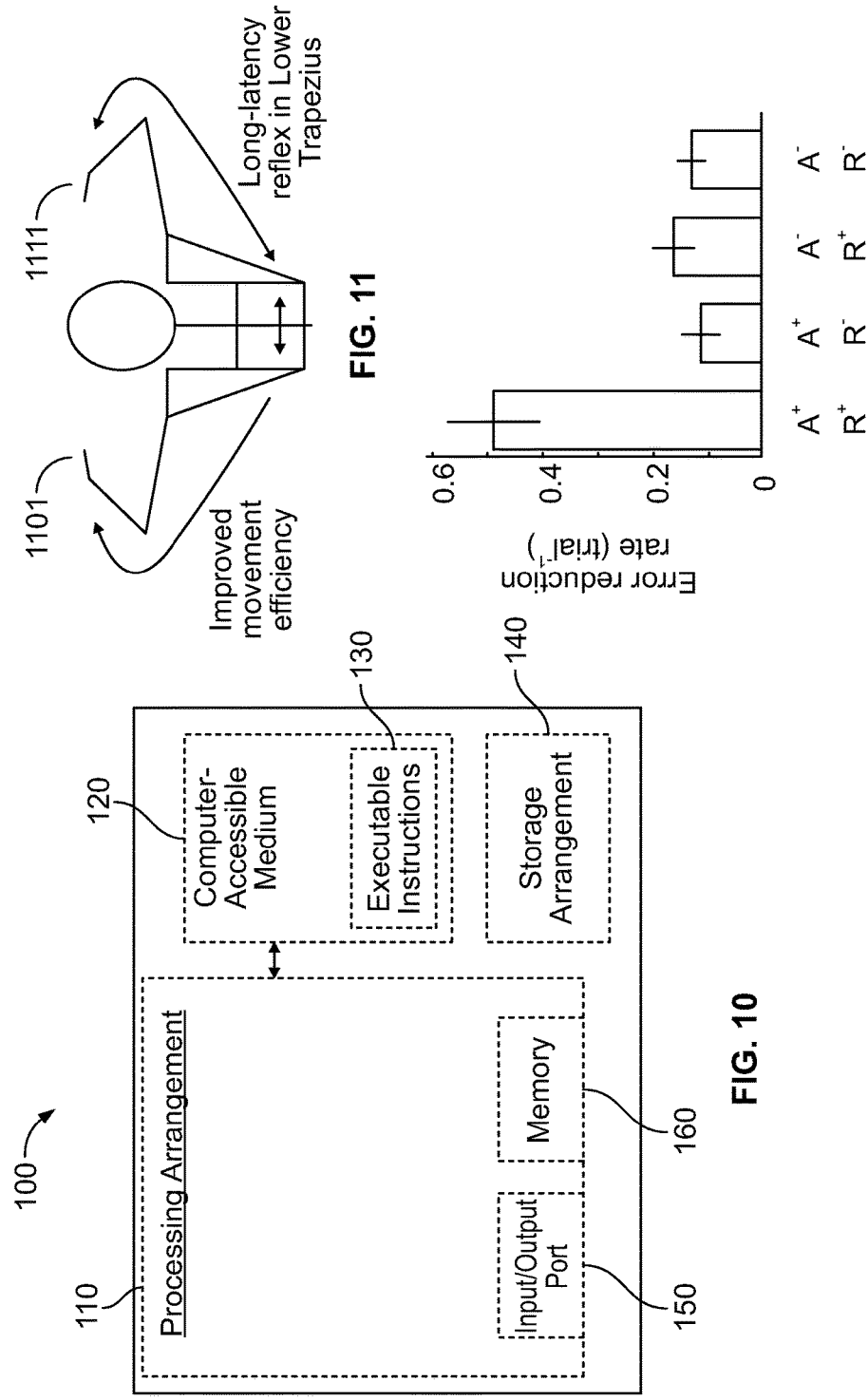
FIG. 10 illustrates an embodiment of a computer system of the present invention.
FIG. 11 illustrates anticipatory muscle activation as it reduces abnormal directional biases and increases grasp efficiency.
FIG. 12 illustrates a graph showing error reduction rates—reflective learning – with adaptation and repetition, with + indicating presence and – indicating absence.

Second, postural strategies are delineated to enhance alternate hand training for increased movement efficiency. Adaptation occurs by detecting error and then correcting for it predictively on subsequent practice. Short-latency spinal reflexes and intrinsic biomechanical properties of muscles contribute to reactive error correction mechanisms which adjust motor output for novel or unplanned movements. These reactive mechanisms are accentuated post stroke due to central disinhibition, leading to spasticity, synergistic movement patterns, inappropriate muscle co-activation, and use of excessive grip forces, all of which reduce the quality of movement-related sensory feedback and affect learning. However, error correction mechanisms also include supraspinal long-latency reflexes that take into account the consequences of the net torques on interconnected joints, and reflect an internal representation of the dynamics of the entire limb. Facilitation of these long-latency mechanisms can generate anticipatory postural responses that may reduce the need for reactive error correction mechanisms (FIG. 11). The affected hand 1101 of the individual in FIG. 11 exhibits improved movement efficiency based upon the methods applied based on the long-latency in the lower trapezius observed in the unaffected hand's 1111 movement.

Stimulation of forearm and hand afferents has been shown to evoke long-latency reflexes in the lower trapezius muscle—a scapular adductor and anti-gravity upper-limb stabilizer. Voluntary activation of the trapezius further increases the amplitude of the long-latency reflex. Tasks that demand greater dexterity produce even larger bilateral responses in the trapezius and other upper limb stabilizers in healthy individuals, but this modulation is disrupted after stroke. Studies on post-stroke reaching have revealed abnormal joint coupling and muscle co-activation patterns that produce inefficient movements. However, these abnormal patterns are modifiable by the use of gravity loading and trunk restraint, suggesting that postural stability can affect the processing of peripheral movement-related proprioceptive information. For example, studies on skilled pianists show that voluntary activation of the lower trapezius muscle, assisted by biofeedback, leads to greater efficiency of finger movements during playing. In addition, recent preliminary data show that lower levels of postural muscle activation are associated with higher grip forces after stroke.

Spasticity and abnormal motor synergies make repetition challenging after stroke. It is believed that activation of anti-gravity upper limb stabilizing postural muscles (e.g. lower trapezius) is associated with increased movement efficiency. Thus, enhancing alternate hand practice with postural muscle activation may reduce abnormal post-stroke directional biases and facilitate repetition of more efficient movements. It is believed that triggering active postural strategies through lower trapezius stimulation will increase grasp efficiency. As further described below, certain implementations measure fingertip forces, arm compensation, and electromyographic (EMG) activity in arm and back muscles to assess directional biases.

Third, certain implementations determine and utilize learning rates across multiple time-scales and stages of skill learning for improvement in hand function post stroke. Adaptation of sensory-motor mappings is a fast learning process, which leads to a rapid reduction in movement error, and typically takes only a few trials; however it is easily forgotten. Repetition, on the other hand, is an error-independent process, and leads to a slow tuning of directional biases toward the repeated movement. For example, the rate of within-session and between-session learning across stages of skill learning with 'enhanced alternate hand training' can be examined and compared to training with the affected hand alone, using a novel task panel and structured training protocols. Successful motor learning requires a combination of fast and slow processes (FIG. 11). Appropriate sensory-motor mappings learned through adaptation must be reinforced over time through repetition across various stages of motor learning. Early learning (Stage 1) is thought to depend on attentional mechanisms. Attention to specific task features or sources of sensory information (e.g. kinesthetic, tactile and visual) at this stage may assist with learning. The next associative stage (Stage 2) is characterized by formation of visuomotor and sensorimotor associations through trial-and-error practice. At this stage, transfer of learning from one limb to the other occurs readily. Associations formed by using the unaffected hand can be used to improve the associations formed with the affected hand. In later learning (Stage 3) the movement is fine-tuned and becomes automatic. This stage of learning would require repeated practice with the affected hand which will lead to greater movement efficiency. Training algorithms are thus developed for each stage of learning.

Certain implementations provide a solution for re-learning of skilled hand function where the individual can learn at their own pace with guidance from the game-based sensorimotor rehabilitator (SMR). The systems and methods enable the individuals to learn to interact with functional objects using just the right amount of force, tilt, finger torques, and muscle activity to regain lost skill.

In one implementation, real objects are customized with force, orientation and acceleration sensors and the object is virtualized on screen. As the individual manipulates the object or objects, visual feedback is provided regarding the appropriateness of fingertip forces, and orientation in a systematic manner to facilitate learning of the correct associations. The force and orientation information is also fed to computational biomechanical models, and software algorithms to inform the thresholds for visual feedback. Further, in certain implementations, wearable position and muscle sensors embedded in a dorsal glove, cuff, sleeve or vest at key areas also send information regarding limb position to the computational models and algorithms. The output of the algorithms is be sent to actuators located on the glove/cuff/sleeve/vest to provide tactile feedback to key areas in the same manner that a teacher or coach would apply a gently touch to provide a cue to move in a certain manner. Tactile feedback will turn on or off when the individual moves within or outside the set parameters of the movement. Real time, trial-to-trial information from interaction with the object can be stored and communicated to the provider's electronic medical record for diagnosis, documentation of progress, and fine-tuning of stimulus parameters and gaming and feedback levels provided through a service provider. Various implementations utilize methods for how and when practice should be facilitated with one hand, or both hands separately, alternately, or simultaneously.

Figure 2:
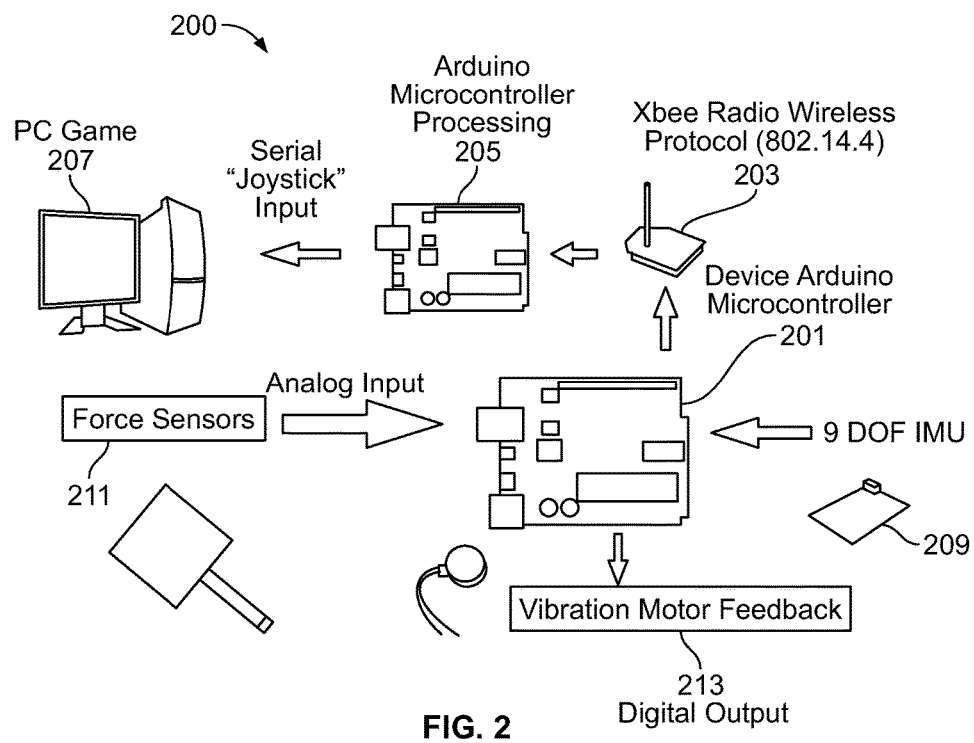
FIG. 2 Parts used to create device components.

One implementation of a device for facilitating rehabilitation and training described above incorporates several components as shown in the flow chart of FIG. 1, using the parts shown in FIG. 2. FIG. 2 shows one implementation of a rehabilitation system 200. A microcontroller 201 is configured to receive sensor information from force sensors 211, which may be part of a game controller physically manipulated by the user. An inertial measurement unite (IMU) is in communication with the microcontroller to provide inertial information, such as gyroscopic, accelerometer, and magnetometer information. The microcontroller 201 is further in communication with a feedback mechanism 213. The microcontroller 201 may also utilize a wireless communication unit 203, such as to communicate with a second microprocessor 205. The microprocessor 201 is ultimately in communication with a computing device 207, such as a P.C. or laptop.

Figure 3:
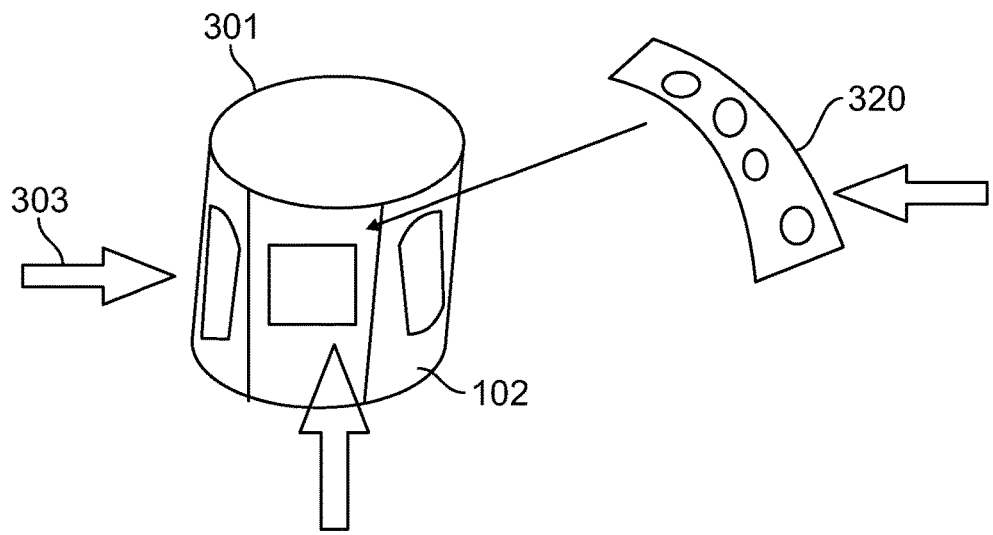
FIG. 3 Sensorized game controller shaped like real objects that need to be manipulated; e.g. a coffee cup, a stick, cooking and eating implements, grooming tools, writing tools, adapted typing and musical keyboards, objects of various shapes, sizes, weights and textures.

In one implementation, the game controller may have a form factor similar to a functional object, such as a coffee cup or ball. In further implementation the controller may consists of an object to be manipulated, such as a cup, and a wearable device for the user such as a vest. The controllers are objects with various shapes and sizes equipped with force sensors, position/orientation sensors, inertial measurement units, and vibrational modules (FIG. 3). FIG. 3 shows a cup-like game controller 301 having a cylindrical body. Force sensors 303, such as force sensitive resistors, are positioned to correspond with a user's hand. For example, the force sensors may be positioned at multiple locations to correlate with fingertip and palm placement on the game controller 301. A separate feedback mechanism 320 is provided, such as a strap or bracelet, to provide feedback regarding the position of the game controller 301.

Figure 8:
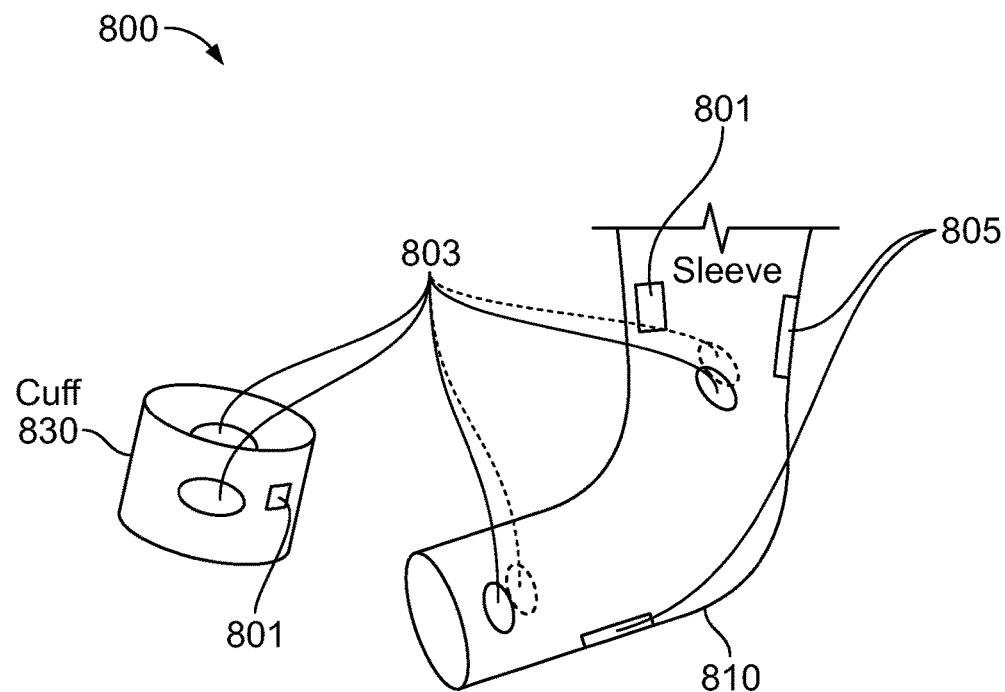
FIG. 8 illustrates a sensorized cuff and a sensorized sleeve.

FIG. 8 illustrates another implementation where the system 800 includes a sleeve 810 as part of the game controller. The sleeve 810 includes position sensors 805 as well as a wireless transmitter 801. The sensors 805 may be positioned to indicate the position of the upper arm and lower arm. Vibro-tactile actuators 803 are included on the sleeve 810, for example on the flexor and extensor portions of the arm. A cuff 830 may also be provided for further vibro-tactile feedback via vibro-tactile actuators 803.

Figure 9:
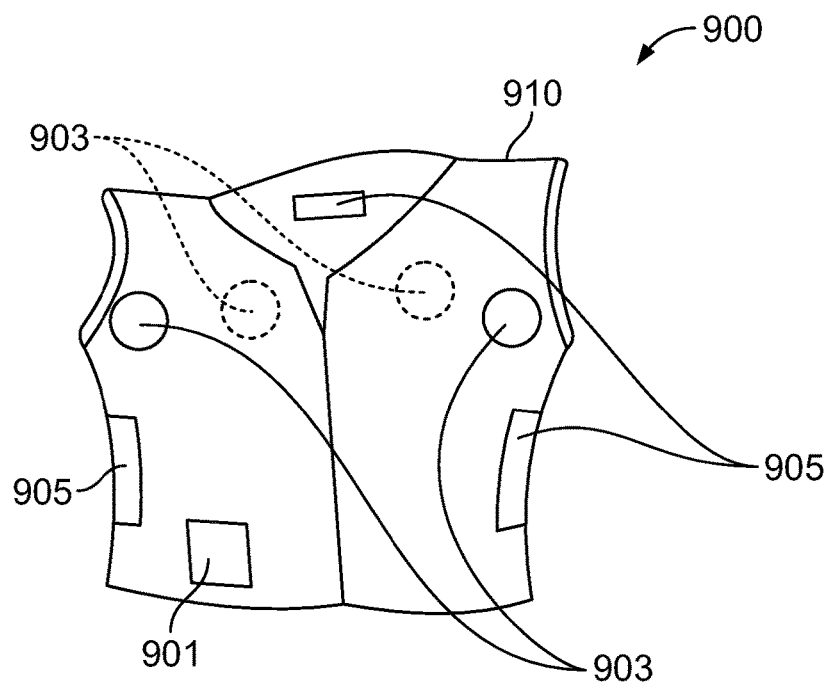
FIG. 9 illustrates a sensorized vest.

FIG. 9 illustrates another implementation where the system 900 includes a vest 910 as part of the game controller. The vest 910 includes position sensors 905 as well as a wireless transmitter 901. The sensors 905 may be positioned to indicate the position of the trunk. Vibro-tactile actuators 903 are included on the vest 910, for example corresponding to the lower trapezius and pectoralis muscle positions.

The force sensors are, in one implementation, oriented orthogonally to measure both grip and load forces, and the rate of change of these forces will be computed. Certain patient specific game controllers include software to communicate, such as wirelessly, to a computer. The information from the sensorized game controller is also integrated with positional and muscle recruitment information from sensors sewn into a cuff/sleeve/vest worn by an individual in certain implementations. The controllers include one or more of sensors and feedback systems. The controllers may be adapted for specific treatment regimes. For example, a controller may provide information to software on an associated computer regarding the grip force, movement speed, and movement direction of an object the user is interacting with. The software may then provide feedback to the user through the controller, such as vibrotactile actuators.

One implementation of the game controller comprises a cylinder similar in size to a coffee cup and instrumented with two pressure transducers positioned at the thumb and middle finger locations and 3D spatial positioning transmitter. Foam or other tactile-deadening material, may be used on the game controller to prevent tactile information for the user, such as to simulate an injury. The micro-computer interface includes circuitry to acquire force data from force transducers and 3D position transducers. The controller communicates wirelessly with the game based software on the laptop that interacts and controls game avatars representing a real-world object. The microcomputer interface and sensors are incorporated within in the controller. The software development uses a 3D game engine's flexible input capacity to drive an interactive visualization of the patient's grip force with game-like reward structures and feedback systems.

Figure 17:
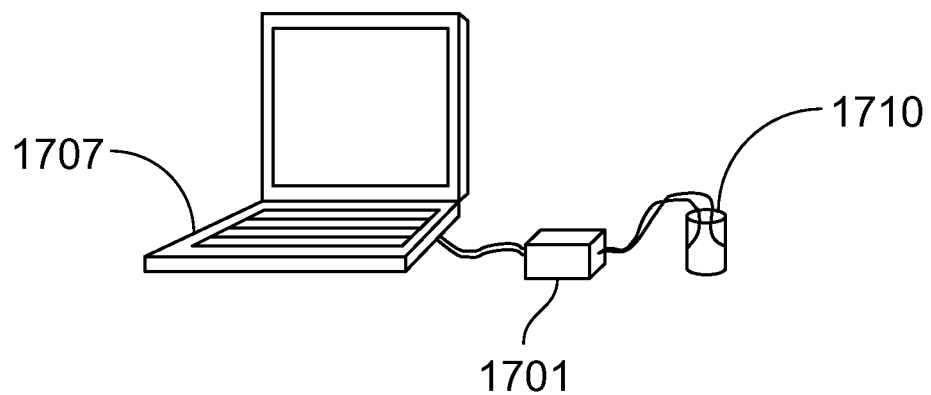
FIG. 17 illustrates an implementation of a system with a computing device in communication with a controller and game device.

As seen in FIG. 17 above, the current prototype's game objective is to ask the individual, represented by an avatar, to squeeze the foam cylinder until the Avatar can open his can of spinach. It will be appreciated that pop-culture or other such references can be used to provide simple clues for the associated functionality as well as familiarity for users. FIG. 17 shows a simplified device layout of FIG. 2, where a system 1701 includes a game controller 1710 in communication with a controller 1701 serving as an interface between the game controller 1710 and a computing device 1707 (shown as a laptop). The microcontroller's imbedded data acquisition code provides for communication, such as continuously monitors the pressure transducer outputs and streams data, to the laptop's game-analysis software that, in turn, controls the avatar and provides an interactive, engaging and fun experience for the patient. In one embodiment, the communication is by USB. The laptop software communicates to the patient using visual and audio cues provided by the game concept. The microcontroller acquires analog voltages associated with pressure transducer response and then transmits raw temporal force data, i.e. force changes over time for each transducer during the training session. Circuitry within the microcontroller a) acquires the analog voltage signals from the pressure transducers; b) performs signal filtering and analog to digital conversion; c) for embodiments using a serial communication transmission, such as RS-232c protocol, the circuitry adds a time stamp to each data pair using the microcontroller's system clock and then transmits the data stream via RS-232C serial format to the laptop. This serial data stream is captured by sub-routines within the laptop's game program that interprets the force and translates it into "Popeye squeezing the can".

In another implementation, interaction with the interactive "cup controller" 1710 provides vibro-tactile feedback in addition to visual and auditory feedback. This version consists of an instrumented "cup controller" 1710 and a wrist band (not shown in FIG. 17) with vibro-tactile actuators. The cup controller 1710 is virtualized on a screen of the computing device 1707 as a cup which needs to be moved in order to catch balls on the screen. As the patient picks up the cup controller 1710, the goal is to learn to use the right amount of finger force to grasp the cylinder and the right tilt. If they squeeze too hard the balls go flying out, if they tilt the cup too far the wristband provides directional vibro-tactile feedback: vibration to the right side of the wrist if the tilt is excessive on the right, and vibration to the left if the tilt is excessive on the other side.

To facilitate training in a systematic and controlled manner, one implementation relates to interactive training algorithms. The training algorithms are based on the principles of 'learning to learn', where learning simple sensorimotor associations within a low dimensional task structure will lead to faster acquisition of similar associations for other tasks. The stepwise introduction of variability and complexity across the stages of learning will then lead to generalization of learning to novel tasks. The training will be delivered using instructions on the computerized display to the user based on input from the sensorized objects and the dorsal glove/cuff/sleeve/vest implementations. The instructions may cue practice with one or the other hand, and provide feedback and reward for correct performance. In one implementation, a sensorized mat is utilized and the training algorithm is adapted for such sensorized mat to facilitate standardized object placement in the work space and a structured progression of training from simple sensory-motor mappings, to practice with more complex real-world objects leading to increased overall skill. The training algorithms may be useful for training hand skill in other patient populations as well.

In one implementation, a video game platform is provided. A game controller is virtualized on screen, and interfaced with game scenarios to provide visual feedback of the interaction with the object and augment the feedback based on the output of the analytic algorithms. The game scenarios will provide interactive and enjoyable training. Game can be viewed on a variety of platforms, e.g. iPod, iPhone, iPad, Laptops, and the controller itself.

Figure 6C:
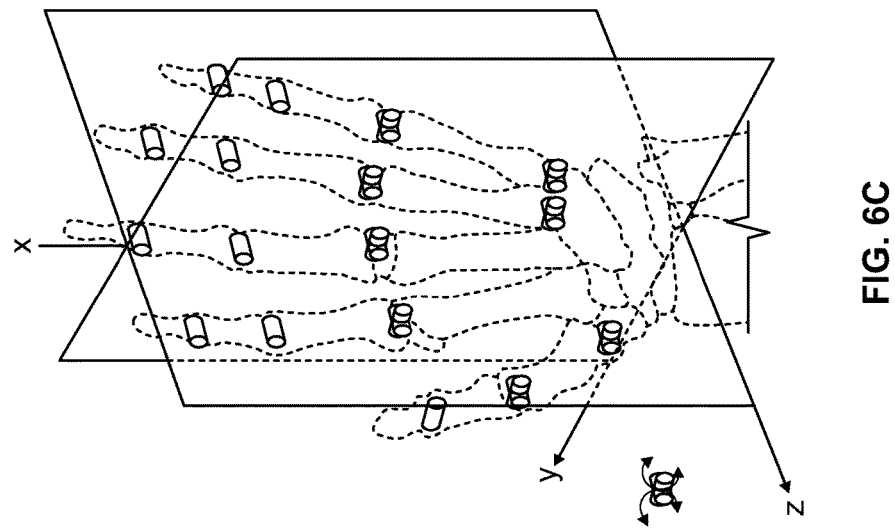
FIG. 6C is a schematic mapping the joints of a hand.
Figure 6A:
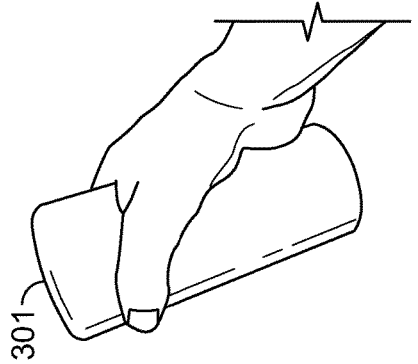
FIG. 6A is an image of a virtual human grasping a cylinder.
Figure 6B:
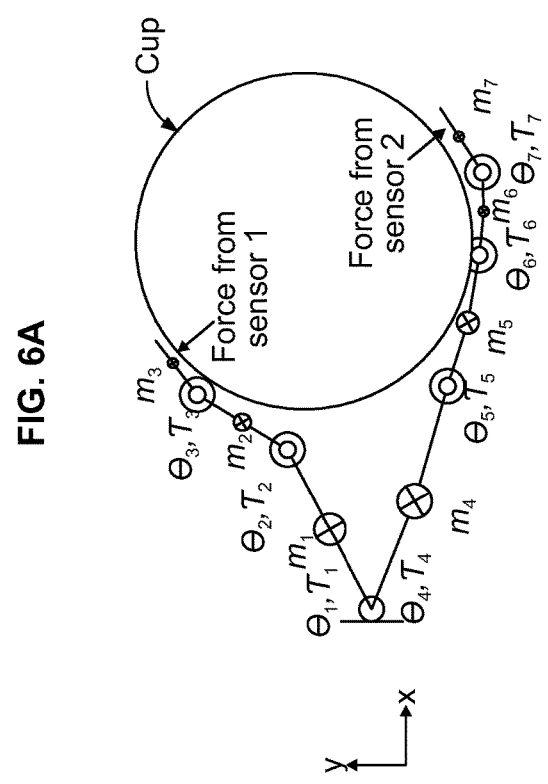
FIG. 6B is a schematic of a finger grasping a cylinder.

One implementation utilizes analytic software. During typical operation, the game controller software will continuously monitor force transducer pressures and acceleration of the object from trial-to-trial from each hand separately for diagnostic information. For example, the user will be directed to modify the object by changing its weight (w), or changing the texture (t) of the object-grasp interface. The user will also be asked to hold the object in various ways to gather information on the finger joint positions to compute estimated torques at the metacarpophalangeal (MCP) and interphalangeal (PIP) joints. FIGS. 6A-C illustrate a hand grasping a cylinder. The information obtained from these directed grasps will be used to set thresholds for visual and tactile feedback.

In one implementation, electronic inputs from position and muscle sensors are embedded in wearable modular garments comprising dorsal gloves/cuffs/sleeves/and a vest at key locations to signal the position, orientation and activity at critical positions or muscle activity levels to provide information about the limb strategy used to manipulate the object. As a patient grasps the object, electronic inputs from the device will be integrated into computational hand/arm models and software algorithms that will (1) integrate information from all the activated sensors on the object and the wearable garment, (2) process the information as detailed below to compute performance parameters, (3) send outputs to actuators located on the glove/cuff/sleeve/vest to activate key areas to provide tactile feedback about how the movement is being performed, and (4) transmit the clinical performance data and analytics to physicians or providers to integrate with the user's electronic medical record.

Figure 18:
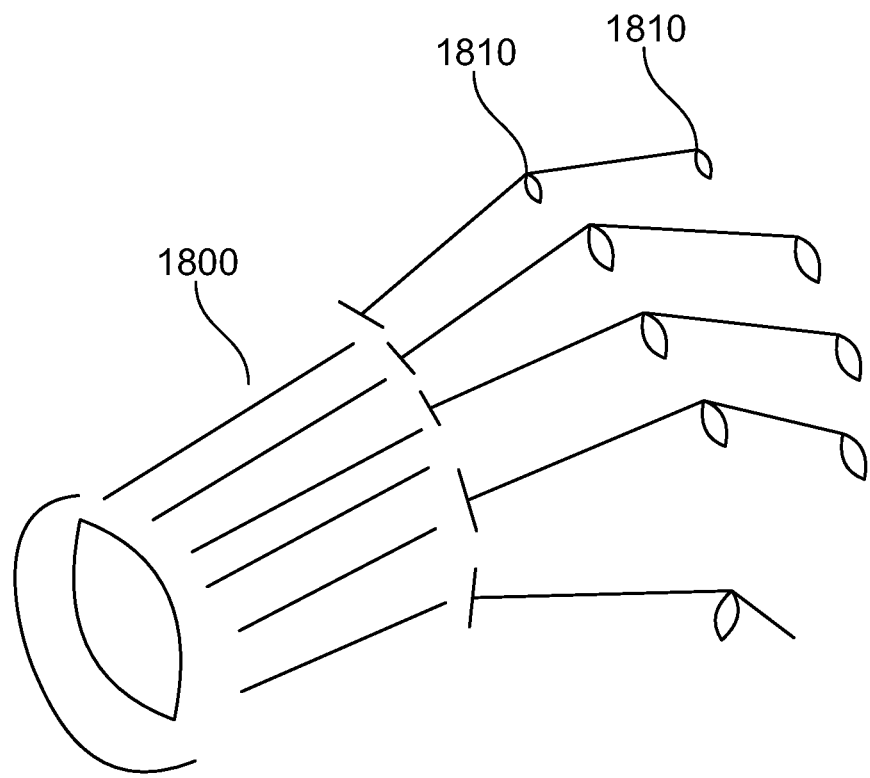
FIG. 18 illustrates an implementation of a dorsal glove.

In one implementation, a dorsal glove 1800, shown in FIG. 18, is utilized. The dorsal glove 1800 rests on the top of the hand. It is fixed to the palmar surface using adjustable bands 1810. In one implementation, the adjustable bands are fixed over the creases of the proximal interphalangeal joints and distal interphalangeal joints. Sensors on the dorsal glove detect finger joint positions and angles of the proximal interphalangeal joints, distal interphalangeal joints, and metacarpophalangeal joints. Vibrotactile actuators embedded on the glove over the knuckles can trigger changes in position to specifically detected positions.

The information provided allows for computation of performance parameters. For example, orthogonally placed force transducers will measure the rate of change of load force (vertical force) and grip force (normal force) which will be used to compute scaling error, or the mismatch between the forces needed to grasp the object and that actually produced. Ideal performance metrics will be obtained from stored normative data of healthy individuals, or "normal" performance from the unaffected limb.

Figure 4:
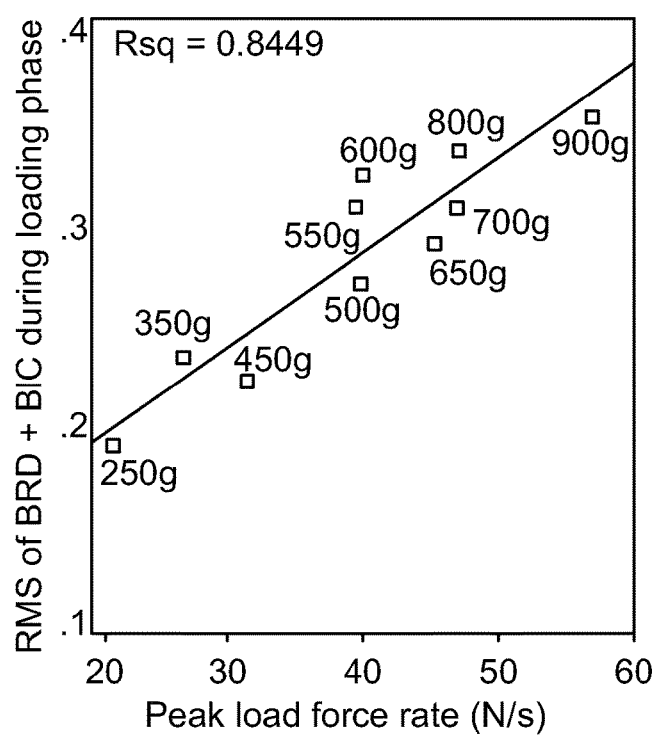
FIG. 4 is a graph illustrating peak load force rate linearly scaled to weight and activity in lifting muscles.
Figure 5A:
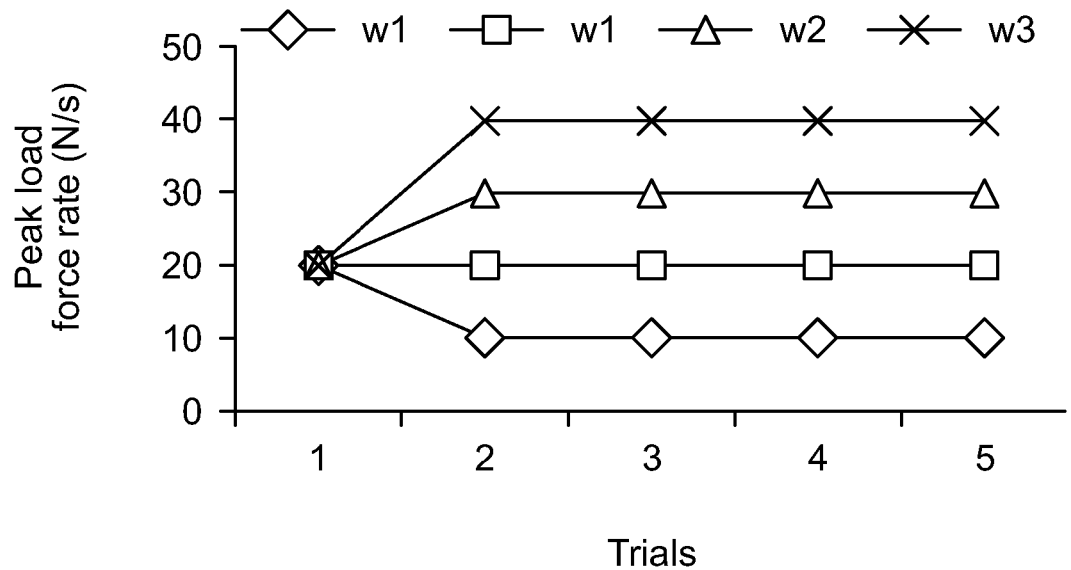
FIGS. 5A-5B illustrates the determination of scaling error for a given trial across weights (FIG. 5A) and trial-to-trial variability (FIG. 5B) to measure successful adaptation and savings.
Figure 5B:
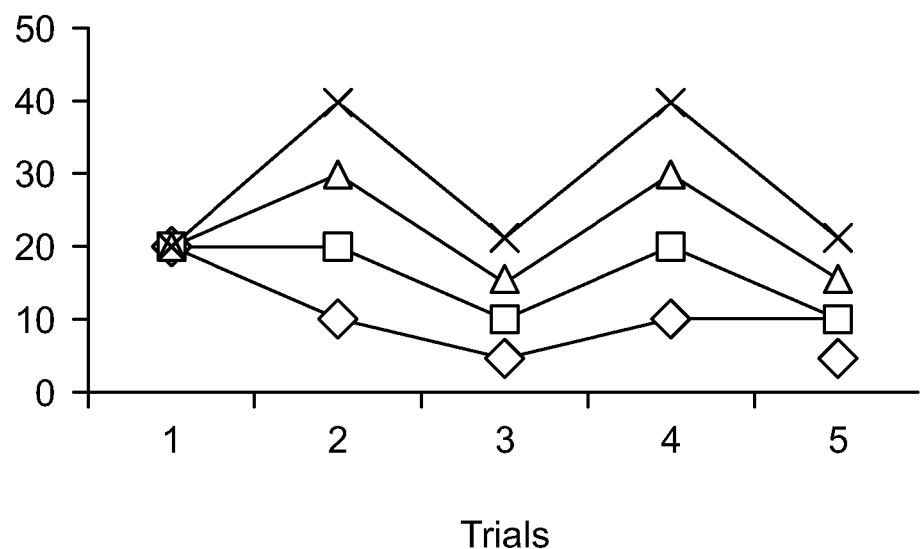

The error definition for any trial is motivated by the ideal case of scaling where, given specific weights, a linear relationship is observed in the peak rate of change of the vertical load force (pLFR, FIG. 4). For a given trial, (e.g. Trial 3 in FIG. 5), the N weights in ascending order are $w_1$, $w_2$, ... $w_N$ with corresponding peak load force rates $F_1$, $F_2$, ... $F_N$. Taking a weight $w_n$ and its associated pLFR, $F_n$ as the reference pair, $w_n$ one can determine the ideal peak load force rates for the other weights $w_k$ as $$F'_k = \frac{w_k}{w_n} F_n,$$

and the mean sum-squared error as $$e_n = \frac{1}{N} \sum_{k=1}^{N} (F_k - F'_k)^2,$$

where the subscript in $e_n$ indicates that the nth weight-pLFR pair is used as the reference unit for the calculation. The scaling error of a given trial j can then be calculated by averaging $e_n$ based on different reference pairs, $$E_j = \frac{1}{N F_{RMS}^2} \sum_{n=1}^{N} e_n,$$

where dividing by the normalizing factor $$F_{RMS}^2 = \frac{1}{N} \sum_{n=1}^{N} F_n^2$$

will allow comparison of the scaling error between sessions when different weights are applied. Within a session, the reduction rate of the scaling error $E_j$, across J trials will be a measure for "successful" adaptation. The scaling error will first be computed during initial diagnostic trials prior to training. The aim of the training session will be to reduce the mismatch in scaling error between the normative data and the real time data, and/or between the "unaffected hand" and the "affected hand" which will be the reference hand data. The peak LFR or peak GFR at each training trial will be compared with the average error for the given weight of the object from the "normal" trials. A mismatch of >50% will signal augmentation of visual feedback on the level of grip force and prompt the individual to practice with the unaffected hand before practice with the affected hand until the mismatch is reduced to <10%. If there is no unaffected hand as the reference hand, mismatch will lead to trigger of vibrotactile actuators in multiple locations on the flexor and extensor aspect across the wrist, the elbow and back (see below). Testing has shown that the mismatch is due to excessive coactivation which can be reduced by location specific vibrotactile stimulation.

For certain implementations, trial-to-trial variability in the magnitude of the pLFR (FIG. 5B) will also be computed independent of the scaling error as the variance of pLFR divided by the weight (to remove the weight effect). Decrease in trial-to-trial variability will precede successful adaptation. Scaling error and trial-to-trial variability will be computed on the peak grip force rate (pGFR) for adaptation to texture over every 5 trials. Higher trial to trial variability is correlated with increased grip forces to increase the safety margin, which indicates difficulty with processing of sensory information from the object. Increased trial-to-trial variability by 50% compared with that from the reference hand will trigger stimulation of vibrotactile actuators in the back of the vest to activate the lower trapezius muscle (FIG. 6) to increase stochastic noise in the system to enhance sensory processing.

Figure 7:
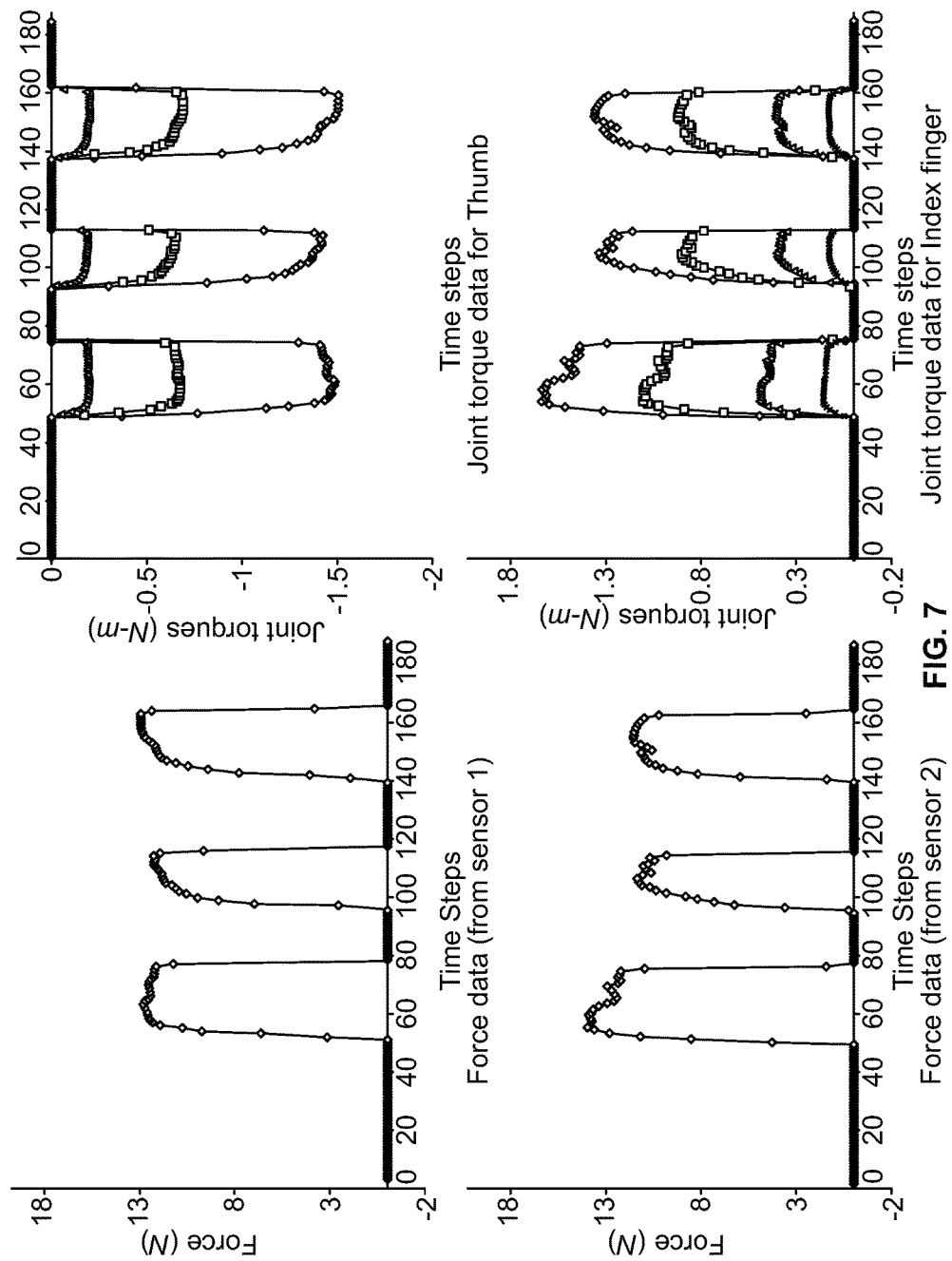
FIG. 7 illustrates graphs of preliminary results with time profiles of measured forces from sensors (left) and torques at each finger joint (right).

In one implementation, figure torques are calculated. The grip force (normal contact force) exerted by each finger, measured by the force sensors, will be used to map to the joint space in a computational hand/arm model, which will output the joint torque at each finger joint (each finger has 3 joints: the distal PIP, proximal PIP, and MCP). The kinetic redundancy of the two fingers due to the muscle-induced actuations in the closed loop will be resolved using an optimization algorithm. Normally the finger torquesare greater at the proximal PIP joint compared with that in the MCP joint (FIG. 7). Greater finger torques in the MCP joints of the fingers compared to the proximal PIP joints signal an inefficient grasp and will trigger vibrotactile actuators in a cuff in the front of the wrist joint to facilitate relaxation of the muscle and change in finger position. Success will be measured by reduction in error between the MCP and PIP joint torques produced by the training hand compared with the same from the reference hand.

In one implementation, in a compensatory limb strategy is utilized. Position sensors on the sleeve at the elbow and side of the vest will indicate whether the elbow is close to the trunk or away from it. If the elbow is away from the trunk and the muscle sensor over the lateral deltoid is activated, it indicates compensation by increasing the angle of the shoulder to orient the hand to grasp the object. This degree of compensation will correlate with excessive tilting of the object. In order to correct the tilt, the user will have to learn to reduce the shoulder abduction angle by bringing the elbow position sensor and position sensor on the side of the vest closer together. When the distance between the elbow and the vest is greater than that in the reference database, vibro-tactile actuators in both locations will vibrate simultaneously and when the distance is reduced, these will stop vibrating indicating that the correct position has been learned. In another embodiment the onset of vibration, rather than the stopping of it, will indicate that the correct position has been achieved.

It should be appreciated that learning across various sessions and stages of learning will be determined by the (1) savings in the time course of error reduction for adaptation to object weight and texture, and (2) change in the location of the finger torque from the MCP joint to the PIP joints which is necessary for precision grasp, and (3) reduction in compensation of the limb position.

In one implementation, the data will be stored and/or displayed in real time to an electronic medical record in the form of trial-to-trial data (graphs), or average data from a training session (in the form of plots and charts). Alternatively, the data may be stored locally with the user, such as in memory associated with a user device.

While the individual interfaces directly with the objects through a novel interactive gaming environment, clinicians can monitor performance measures, which will be used for both immediate online feedback with or without the presence of an expert available remotely, and/or saved offline as part of the patient training records. This will enable analysis of the training session online and offline.

In one implementation, a wearable feedback device is provided. The wearable feedback device may be a vibrotactile feedback device, embedded in one or more of a dorsal glove, cuff, sleeve, or vest. Snug-fitting band, sleeve and vest or a combination of these in the form of a jacket available in various sizes will have pockets for placement of position sensors, vibro-tactile actuators and wireless muscle and movement sensing transmitters in specific locations indicated in FIG. 8 and FIG. 9. The actuators will be located on the flexor and extensor aspect and will turn on or off based on the output of the software algorithms. In one implementation, the actuators will communicate wirelessly with the electronic interface from the sensorized object and the gaming platform providing an interactive experience and feedback to aid in rehabilitation.

Certain implementations include methods to facilitate hand-object interactions and rehabilitation. It is believed that the systematic facilitation of controlled hand-object interactions assists in the formation of specific sensory-motor associations in neurologically impaired individuals. The configuration of the training algorithms in conjunction with information from the various sensors will prevent the use of compensatory strategies such as gripping the object too tightly or tilting it too much by providing tactile stimulation in key areas. It will facilitate practice with one or both hands separately, alternately, or simultaneously. Tasks and stimulus features can be programmed and presented to the individual using virtual reality and updated based on trial-to-trial performance. These methods can be used in conjunction with peripheral or central electric stimulation to reinforce new movement patterns.

In one application, the device may be utilized with a healthy individual for training rather than rehabilitation purposes. Ideal placement of a hand, for example, can be modeled and feedback provided when the hand varies from this model. As one example, placement of hands during piano playing can be monitored to provide feedback on physical orientation and hand posture that may not be evident merely from the notes being played.

In one embodiment, shown in FIG. 10, a system 100 is provided. FIG. 10 shows an exemplary block diagram of an exemplary embodiment of a system 100 according to the present disclosure. For example, an exemplary procedure in accordance with the present disclosure can be performed by a processing arrangement 110 and/or a computing arrangement 110. Such processing/computing arrangement 110 can be, e.g., entirely or a part of, or include, but not limited to, a computer/processor that can include, e.g., one or more microprocessors, and use instructions stored on a computer-accessible medium (e.g., RAM, ROM, hard drive, or other storage device).

As shown in FIG. 10, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

1. Experimental Results

The co-ordination of fingertip motion and forces during object manipulation developed by Johansson et. al has served as a model system of sensorimotor integration for more than 30 years, and is a sensitive test of fine motor control in various patient populations. Experiments were built from this work to understand the mechanisms of hand motor impairment after stroke and design physiologically-based rehabilitation approaches. The following experiments test the 'alternate hand training strategy' which involves practice with the unaffected hand and then the affected hand, to facilitate adaptation, repetition and relearning to restore hand function in stroke patients. The first step is to determine how individuals adapt their grasp under various sensory constraints, i.e. presence or absence of kinesthetic, visual and tactile sensory modalities. This would provide a bench mark, which can then be used to test under which conditions the alternate hand training strategy will restore adaptation.

a. Training Methods

A foam coating for the fingers effectively impairs tactile sensibility and eliminates 2-point discrimination in healthy individuals. One experimental protocol was fully developed as show below (Table 1 below).

TABLE 1

Experimental protocol for Aim 1

| | Kinesthetic | Vision | Tactile | Experimental Conditions |
|---|---|---|---|---|
| 1 | 1 | 1 | 1 | full vision |
| 2 | 1 | 0 | 1 | vision occluded |
| 3 | 0 | 1 | 1 | no lift |
| 4 | 0 | 0 | 1 | vision occluded + no lift |
| 5 | 1 | 1 | 0 | foam fingers |
| 6 | 1 | 0 | 0 | vision occluded + foam fingers |
| 7 | 0 | 1 | 0 | no lift + foam fingers |
| 8 | 0 | 0 | 0 | no lift + vision occluded + foam fingers |

Linearity between variables measuring grasp adaptation and object weight and texture and select weight and texture pairs. FIG. 19A-B show a linear relationship between the peak load force rate and object weight for a wide range of weights (n=10), and between peak grip force rate and the friction at the grip surface (measured by the co-efficient of friction, COF) for a wide range of textures (n=14). Equivalent weight and texture pairs were selected and their presentation randomized in the experimental protocol. FIG. 20A-B show that the selected weights and texture pairs show relatively similar differences in peak force rates.

Minimize the noise in grip force data due to changes in humidity and temperature. Grip forces are extremely sensitive to small changes in humidity and temperature. The ridges on the fingertips serve to increase the coefficient of friction at the grip surface which then requires smaller grip forces to grasp the same object. This poses a challenge when subjects are performing repeated lifts over a period of time even when room temperature and humidity are controlled. Therefore a thin film (e.g. Tegaderm) may be applied over the fingertips. Tactile sensibility can be measured by examining the correlation between the coefficient of friction and the grip force rate (as shown in FIG. 19A-B). The coefficient of friction can be determined for each individual by computing the inverse of the Slip Ratio [ratio of grip force to load force)]. FIGS. 21A-C show the relationship between the slip ratio and the peak grip force rates for a wide range of textures. Note that the slip ratio is in a narrower range when using bare hands and when grasping the objects with a thin film of Tegaderm over the fingertips. The stronger correlation between the slip ratio and the peak grip force rate suggests that tactile sensibility was less impaired by Tegaderm, than with the foam coating, which clearly impaired tactile sensibility as can be seen from the significantly weaker correlation.

b. Preliminary Results:

i. The Alternate Hand Practice Strategy can Restore Adaptation of Fingertip Forces after Stroke.

Figure 13A:
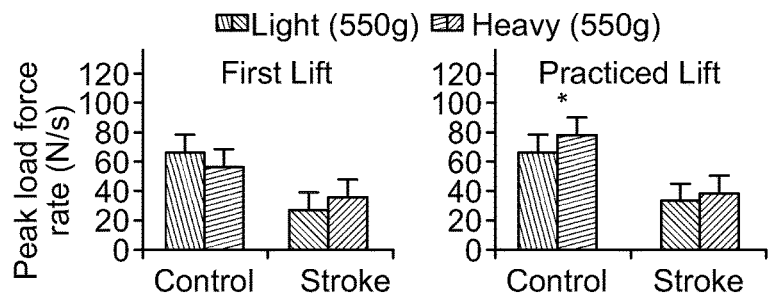
FIGS. 13A-C illustrate congruent hand practice impact on adaptation restoration and muscle control in the affected hand post-stroke.
Figure 13B:
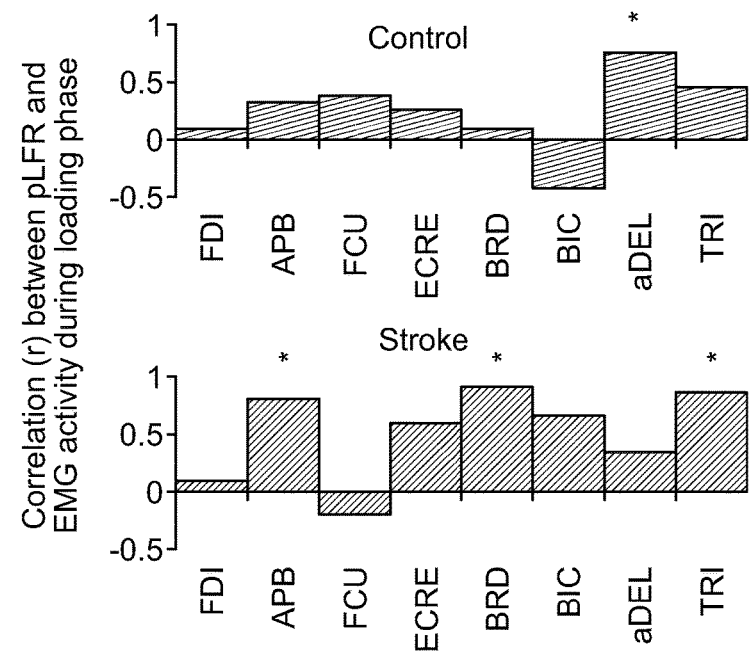
Figure 13C:
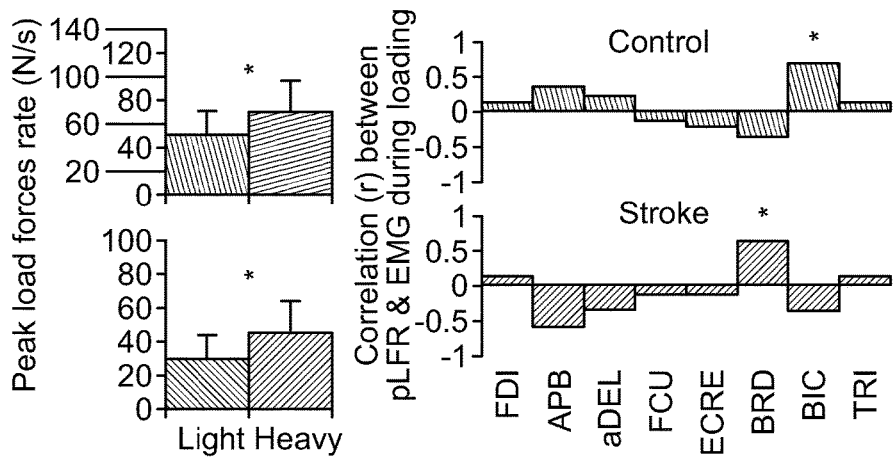

Adaptation with the affected hand is impaired after stroke, but it can be temporarily restored after prior practice with the unaffected hand. The mechanisms underlying lack of adaptation of fingertip forces to object weight [measured by the difference in peak load force rate (pLFR) for two weights] were examined by considering muscle activity using surface and intramuscular (from FCU, ECRL & BRD muscles to avoid cross-talk) electrodes. 14 patients with post-stroke hemiparesis and age-matched controls lifted an instrumented grip object equipped with force sensors. On the first lift, the pLFR was not scaled to weight either in controls or in patients (FIG. 13A, light and heavy bars of similar height), suggesting that the association between object weight and fingertip forces was not learned yet. However, by the $5^{th}$ lift, controls clearly scaled the pLFR showing evidence of adaptation, but patients did not. Both patients and controls lifted a range of weights in this manner. Then pLFR was correlated with muscle activity for the $5^{th}$ lift. In controls, the pLFR was highly correlated only with activity in the lifting muscle—the anterior deltoid (aDEL) (FIG. 13B), since the object was lifted by flexing the shoulder. In contrast, patients showed high correlation with activity in many opposing muscles. When patients first practiced lifting the grip object with their unaffected hand (5 trials) and then with their affected hand (alternate hand strategy), they were able to scale the pLFR on the first trial with the affected hand with corresponding restoration of selective muscle activation patterns as in controls (FIG. 13C). This occurred, however, only when the same action (congruent action) was performed with each hand. These results suggest that successful adaptation to object weight with the affected hand requires accurate kinesthetic information from lifting actions. However, when subjects lifted familiar objects of different weights (e.g. water bottle, soda can) that provided additional tactile and visual information regarding their weight using the alternate hand strategy, neither controls nor patients transferred the ability to scale their pLFR on the first lift with the affected hand. Patients and controls used congruent actions with both hands and were explicitly told that the weight of the objects were the same for each hand. The results suggest that competition among multiple sensory contexts can interfere with the acquisition of accurate internal representations for adaptation to one sensory context. It is believed that training protocols for sensorimotor adaptation must initially be structured within single sensory contexts for successful learning. The above results suggest that restoration of adaptation requires accurate modality specific sensory information, which can be obtained from the unaffected hand.

ii. The Role of Postural Muscle Activation on Movement Efficiency

Figure 14A:
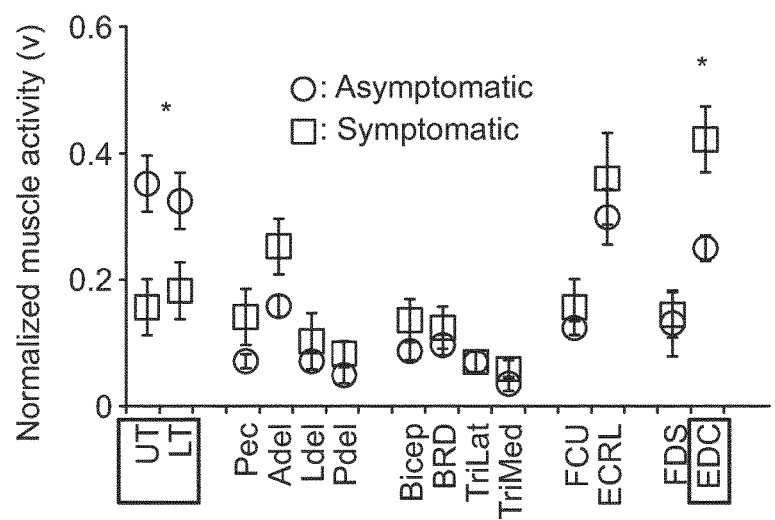
FIGS. 14A-B illustrates symptomatic pianists showing reduced activity in the upper and lower trapezius (LT) and increased activity in the finger extensor (EDC) at baseline compared with asymptomatic pianists. With LT activation, the slope (m) between EDC and LT in symptomatic pianists shifts closer to asymptomatic group compared to baseline (b).
Figure 14B:
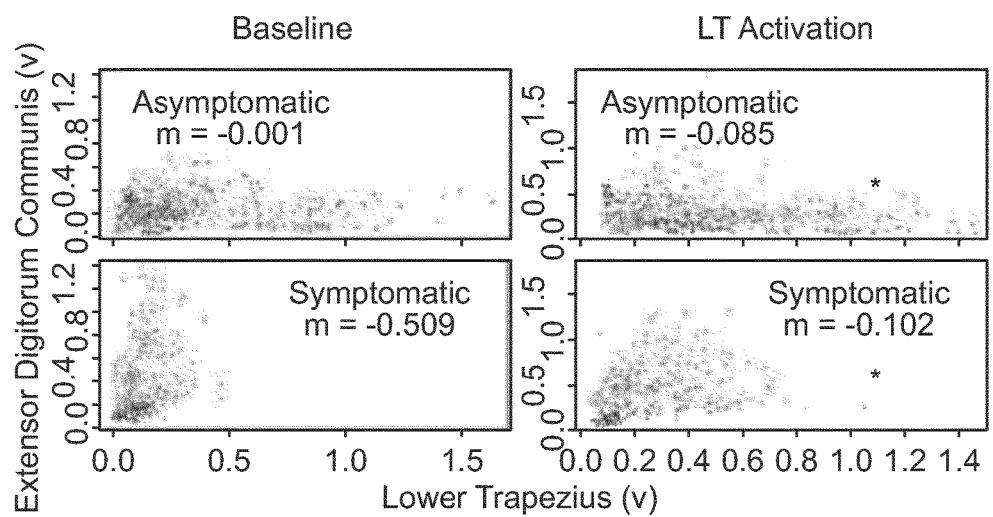

To understand the role of postural muscle activation on movement efficiency 31 expert pianists with and without symptoms of overuse injury were studied. Surface EMG was recorded from 14 upper limb muscles when they played octaves at baseline and with biofeedback-assisted activation of the lower trapezius (LT). Symptomatic pianists (n=11) showed reduced activation in the upper and lower trapezius and over-activation in their finger extensor muscle (EDC) at baseline compared to asymptomatic pianists (n=20) (FIG. 14A). The slope (m) between the EDC and LT (each color cluster represents trials from one subject) was markedly positive in symptomatic pianists, in contrast to a negative slope in the asymptomatic group, suggesting an inverse relationship between EDC and LT muscles. Voluntary activation of the LT muscle shifted the slope in the symptomatic group closer to that of the asymptomatic group compared to Baseline (FIG. 14B, see starred plot), suggesting reduced activity in the EDC muscle and greater efficiency of finger movements. Thus, activation of anti-gravity postural muscles, i.e. the lower trapezius, can improve movement efficiency.

Figure 15:
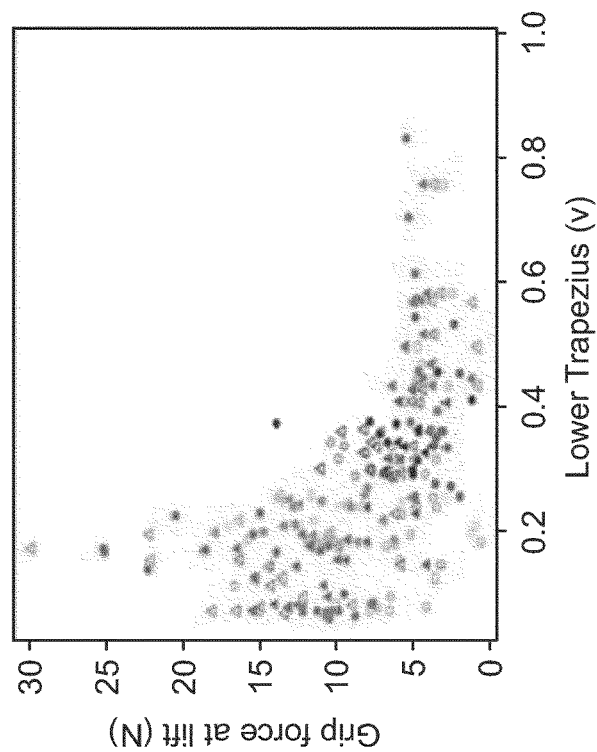
FIG. 15 is a graph of the relationship between lower trapezius activity and grip force at lift during grasping with the affected hand post-stroke.

Based on the above results, further experiment sought to determine if a relationship exists between lower trapezius activity and excessive grasping forces. Patients with stroke have been shown to produce excessive grip forces in both the affected and unaffected hands leading to grasp inefficiency. As described below in Section 3 the subjects (each color cluster represents trials from one subject) who showed greater activity in the lower trapezius produced lower grip forces at lift (FIG. 15), i.e. just enough force to hold the object, but not too much as to squeeze it, suggesting greater grasp efficiency. No intervention was applied to voluntarily activate the lower trapezius. It is believed that grip force magnitude at lift is a meaningful measure of grasp efficiency that may be altered by changes in postural muscle activity.

iii. Feasibility of Alternate Hand Training to Improve Hand Function Post Stroke.

Figure 16A:
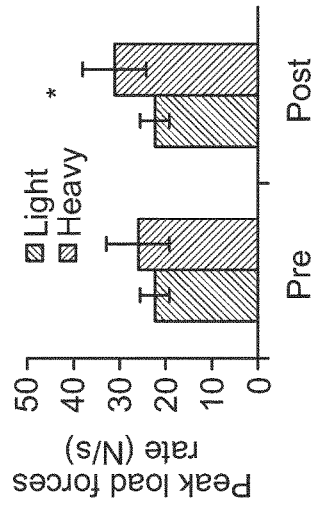
FIGS. 16A-16B illustrate graphs of alternate hand training improving the adaptation of fingertip forces to object weight ratio FIG. 16A and grasp execution FIG. 16B.
Figure 16B:
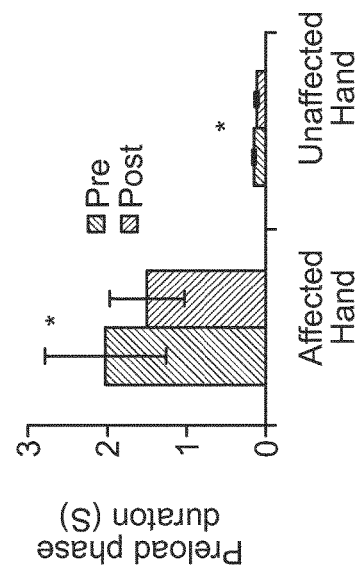

Six subjects with post-stroke hemiparesis participated in a 4-week alternate hand training intervention. Training consisted of eight 45-minute sessions conducted twice a week for 4 weeks when patients grasped and lifted everyday objects first with their unaffected hand and then with the affected hand, in a 1:1 alternating manner, by isolating movement at the shoulder, elbow or wrist joints. Training was progressed to more difficult grasp orientations, using heavier or lighter objects, and combining grasp and lift with transport and placing movements to simulate real world tasks. The goal of training was to attain symmetrical grasping patterns with the two hands. Subjects grasped and lifted an instrumented grip device pre- and post-intervention. Adaptation of fingertip forces to object weight was assessed by the difference in peak load force rates for the light and heavy weights (FIG. 16A, see also FIG. 13) and clearly improved post intervention. Grasp execution was assessed with the preload phase duration (PLD) which is the time taken to stabilize grasp and reflects grip-load coordination. The PLD has been found to be a robust and sensitive measure of grasp impairment post stroke that correlates with several tests of hand function. Although the patients still had considerable impairment, the PLD showed significant improvement post intervention in both the affected and unaffected hands (FIG. 16B). Subjects also showed clinical improvement in tactile sensibility, higher order sensory integration (stereognosis and 2-point discrimination), pinch strength, timing on fine motor tasks (8-13) of the Wolf Motor Function Test and quality of life measured with the Stroke Impact Scale (Table 2).

TABLE 1

Improvement with Alternate Hand Training

| Test | Pre (m ± s.e.) | Post (m ± s.e.) | Comment |
|---|---|---|---|
| Monofilament test of fingertip pressure sensitivity | 3.50 ± 0.60 | 4.30 ± 0.34 | Increased tactile sensibility |
| Moberg score: time to identify objects by stereognosis (s) | 1.73 ± 1.10 | 0.34 ± 0.15 | More objects were identified faster |
| Static 2-point discrimination | 4.44 ± 0.89 | 2.22 ± 0.50 | Improved 2-point discrimination |
| Pinch strength (g/cm$^2$) | 2.89 ± 0.78 | 3.61 ± 0.99 | Increased pinch strength |
| WMFT tasks 8-13 (s) | 42.09 ± 13.32 | 39.09 ± 10.71 | Slightly faster performance |
| Stroke Impact Scale | 230.50 ± 9.86 | 260.50 ± 9.66 | Improved quality of life |

The above results demonstrate the feasibility of alternate hand training for clinically relevant improvement in hand function.

2. Mechatronic Rehabilitation Device

In one embodiment, the game controller is a mechatronic device for aiding in diagnosis and rehabilitation including forces sensors that measure not only grip forces but load forces. This embodiment of a rehabilitation device allows for gathering of information regarding both the lifting force and the gripping force exerted by the user. In one embodiment, the rehabilitation device comprises sensors and electronics for the purpose of grip and load force scaling, for example flexiforce sensors and Arduino Uno powered by ATMega328 microcontroller.

The rehabilitation device operates on the principles of mechanics, the weight of the body measured by a weighing scale is equal to the net upward normal force acting on the body. Upon application of an upward force on the body, the normal force acting upwards becomes the weight of body subtracted by the force applied in upward direction. Using this concept, the device is capable of measuring the load force, and the corresponding load force rate.

$$F_{net}=Mg-F_p$$

Figure 29A:
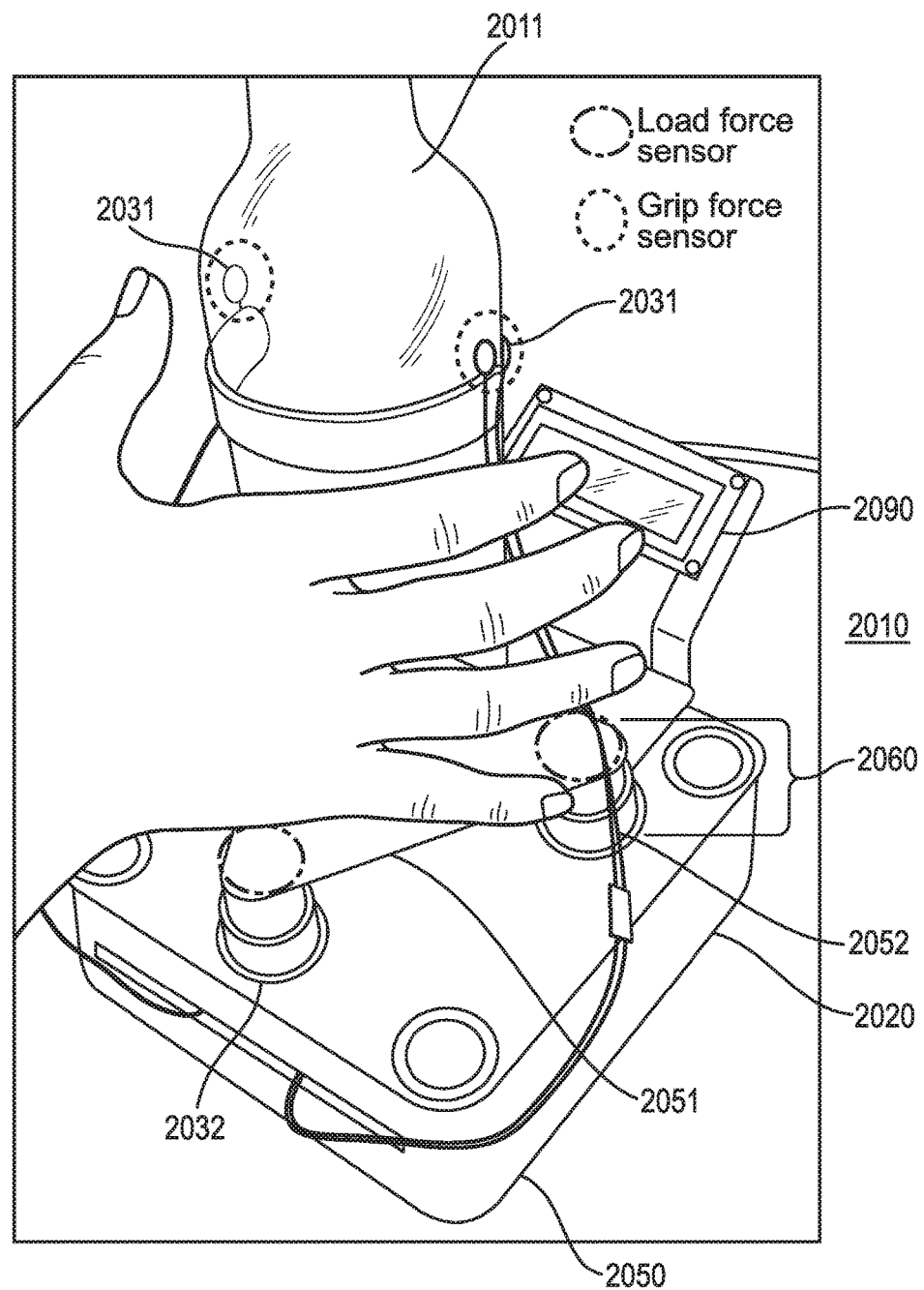
FIG. 29A shows a prototype of the interactive task platform and FIG. 29B shows a display for training of adaptation of grasping and lifting forces.
Figure 29B:
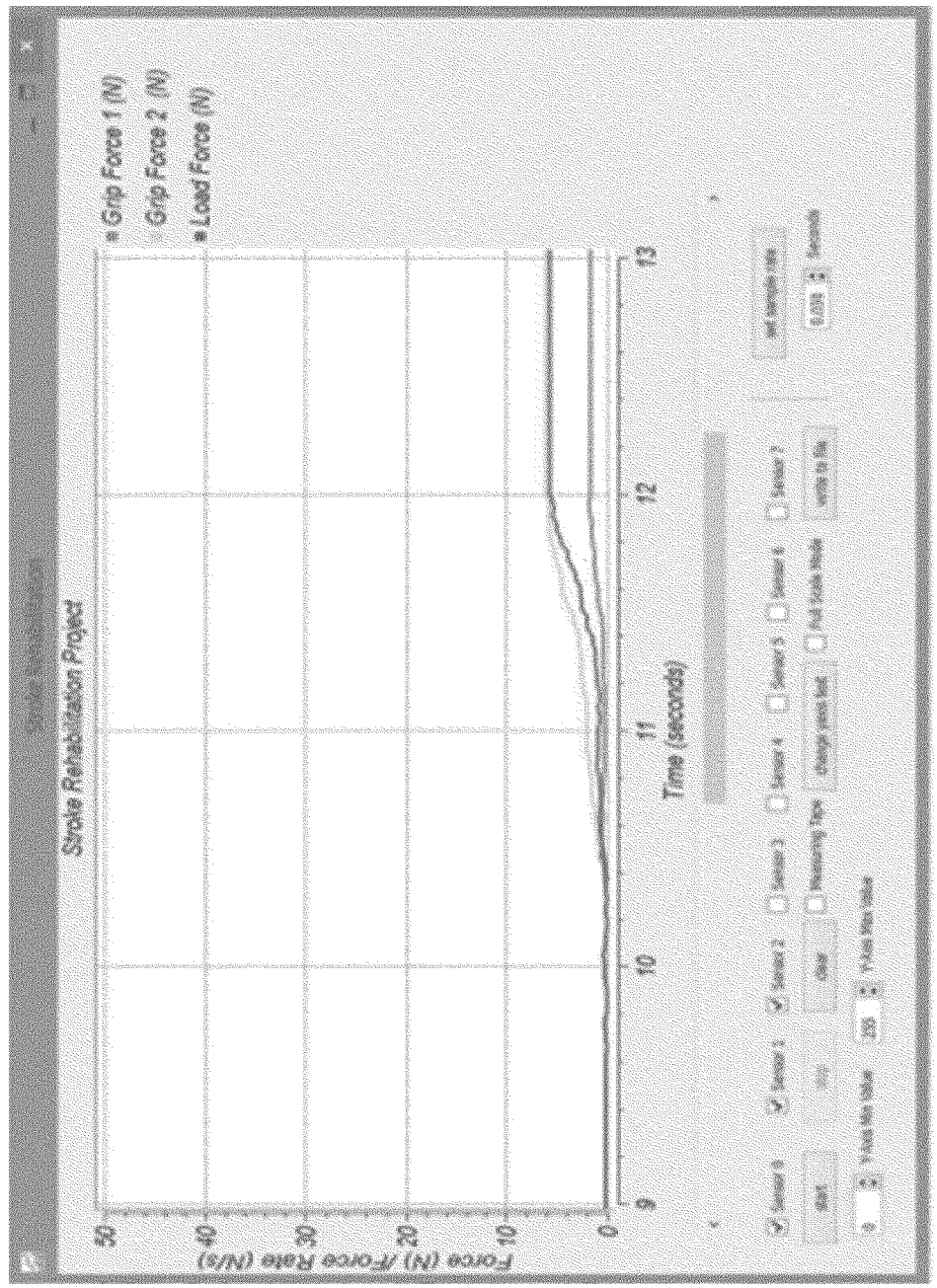

$F_{net}$=>Net forces acting on the body, M—Mass of the object, g—gravity, $F_p$—Force applied by patient.

a. Device Construction:

One embodiment of a rehabilitation device 2010 consists of a housing 2020, a grasping object 2011, a base 2050, and at least two force sensors 2030. FIG. 29 illustrates one such embodiment. In a preferred embodiment, there are between two and ten sensors 2030, such as Flexiforce sensors. In a particular embodiment, a force sensor 2030 corresponds to each finger of a user's hand. For example, two sensors 2030 are 9.53 mm in diameter and the remaining three are 25.4 mm in diameter. The force sensors 2030 comprise two or more types of force sensors. In the example embodiment with different sized sensors 2030, the smaller sensors are used for grip force measurement 2031 and the larger sensors are used for load force measurement 2032. In one embodiment, the load sensors 2032 are included on the grasping object 2011 and the load sensors 2032 are positioned on either the base 2050 to receive the grasping object 2011 or on the grasping object 2011 to engage the base 2050.

In one embodiment, the rehabilitation device 2010 includes a glove 1800 that includes the sensors 2031. The glove 1800 may be affixed to the grasping object 2011 or separate but engageable therewith. A glove is shown in FIG. 18.

In one embodiment, the smaller sensors 2031 are attached to the thumb and index finger of the glove 1800. This is adjusted to fit the subject's fingers accurately using a fastener (such as hook-and-loop) arrangement. This helps the sensors 2031 to coincide with the area of contact between fingers and an object. In one aspect, the glove 1800 includes components so as to be interchangeable between the two hands of the subject. This arrangement satisfies the friction requirement for the appropriate grasping of objects. For embodiments with a glove 1800, the grasping object 2011 can be an everyday object such as a soda can, coffee cup, ball, etc. Placing the grip sensors 2031 on the glove allows grip force data to be gathered without the need for specialized grasping objects. Placing the load sensors 2032 on the base 2050 allows load information, including weight of the grasping object 2011, to be determined without the need for specialized grasping objects.

The base 2050 may include a coaster 2051 for receiving the grasping object 2011. In one embodiment, the base 2050 includes, such as, in FIG. 29A, a triangular coaster 2051 with three legs 2052, which rests on the force sensors 2035. The base 2050 may rest on a device stand 2060 that is part of the base 2050. In the embodiment of FIG. 29A, there are three larger diameter load sensors 2032. These sensors may be of any acceptable type, including 3-D printed as shown in the embodiment of FIG. 29A. The grasping object 2011 to be lifted by the patient, such as a soda can or a water bottle, or a systematically weighted apparatus is placed on top of the base 2050, on the coaster 2051 and the experiment is performed. The legs 2052 may be used to provide an adjustable height, but also serve to focus the load force on the load sensors 2032. The shape of the coaster 2051 and the number of legs 2052 may be varied as appropriate based on the size, mass, and shape of the intended grasping object 2011. The load force sensors' 2032 results are summed to calculate the applied load on these sensors 2032.

Figure 22:
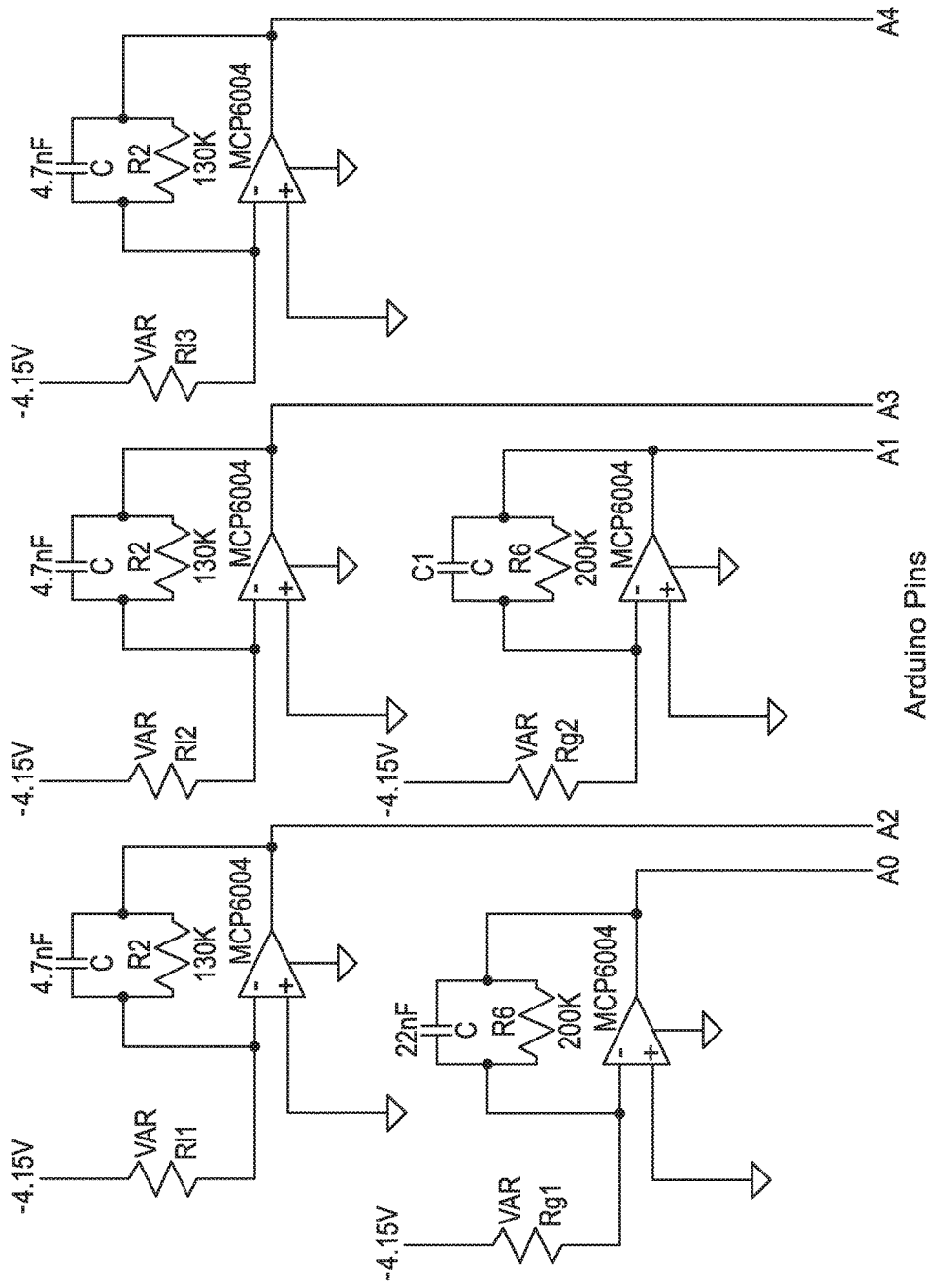
FIG. 22 is a circuit diagram of one embodiment of a mechatronic rehabilitator.

In one embodiment of a rehabilitation device using an Arduino board, the output voltage of sensors 2030 are connected to an operational amplifier circuit MCP6004 functioning in inverting mode. The output of op amp's voltages are measured by the Arduino analog pin. The measured voltages are converted into corresponding force measurements by Arduino, through Linear Regression and serially sent for plotting in the computer. The Arduino calculates the corresponding load force rates and grip force rates that can be plotted in python as well as Matlab®. The rehabilitation device 2010 also facilitates a Parallax LCD display 2090 to interactively display the grip forces and load to be lifted. The rehabilitation device 2010 may include a start button and an auditory cue beeper, for example positioned on the base 2050. While a button (not shown) or other manual mechanism for initiating the device 2010 can be provided, the device 2010 may also be automatically started though the use of motion sensors, capacitive sensors, or the like, including through the use of sleep and wake modes of operation as standard in modern electronic devices. The various mechanisms for starting the device's 2010 ability to measure forces via the sensors 2030 will generally be referred to as "start button". FIG. 22 illustrates one exemplary circuit that can be used with the rehabilitation device 2010.

When the start button is pressed, preferably the device 2010 indicates the subjects with an auditory cue that the experiment has begun. The device 2010 is smartly programmed to begin the experiment only if the load sensors 2032 detect a grasping object 2011. In one embodiment, the device 2011 will only begin an experiment mode if a force equal to or greater than a threshold, such as 100 grams, is detected. Arduino senses data from the connected sensors and converts the voltage readings to corresponding forces and calculates the load force rates and grip force rates over 35 ms and returns the data through USB to the computer. A software serial is used to connect the Arduino and Parallax LCD. The grip forces applied by the fingers and the remaining load to be lifted by the subject in grams are displayed on the LCD display.

The load sensors 2032 measure the weight of the object. The initial weight of the object is saved as an initial constant. During the experiment the load sensor 2032 values are subtracted from the initially saved weight in order to compute the load force applied by the subject.

The data received through the serial communication is plotted in real-time, such as with Matlab® and Python® interfaces. A comparative study established between Matlab's® sampling rate and Python's® sampling rate found that Python® could sample data faster than Matlab-Arduino IO software interface. Moreover, an end-user interactive gaming interface is being developed and Python® is opted to facilitate a gaming interface development. The game being developed interactively shows the subjects their progress in lifting experiments performed. This type of interactive interface also facilitates data extraction in the background for processing and benchmarking patients' progress in rehabilitation studies.

Figure 23A:
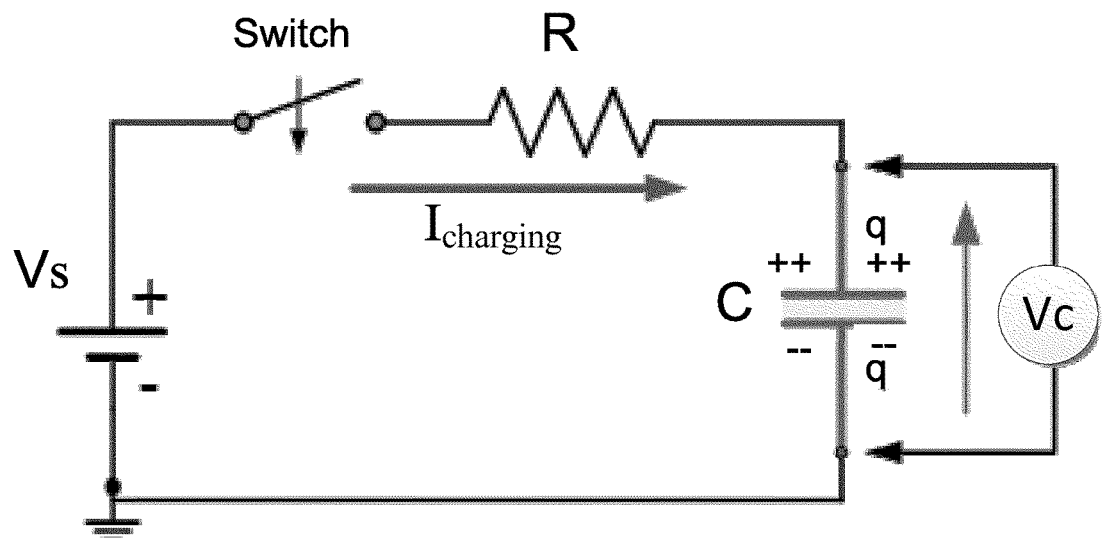
FIG. 23A illustrates an electrical circuit with a switch.

The sensors 2030 should be calibrated to provide the best results. The sensors 2030 exhibit a linear relationship between Force and Conductance. With this concept a preliminary design was conceived considering the Resistance-Capacitance timer circuit. This circuit incorporates RCTIME command in Basic Stamp 2e to evaluate the conductance. The Basic Stamp is powered by PIC microcontroller. The peak baud rate of Basic Stamp was 9600. The sampling rate was lower than expected in this design. The circuit is shown in FIG. 23A. For the illustrated circuit:

$$\frac{V_c(s)}{V_s(s)} = \frac{1}{RCs+1} \Rightarrow \tau = RC$$

Figure 23B:
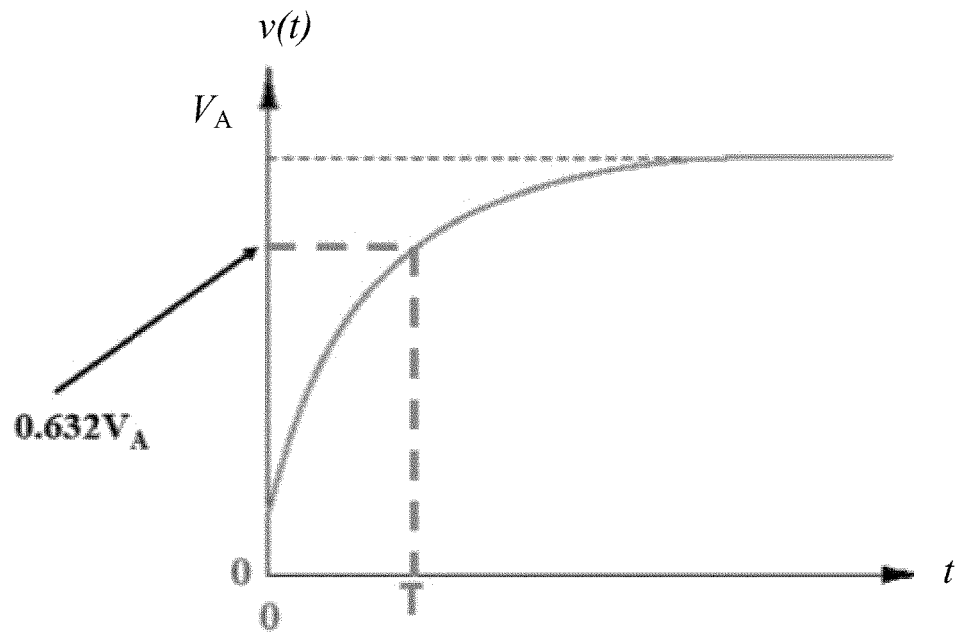
FIG. 23B illustrates a graph for the performance of the circuit of FIG. 23A.

FIG. 23B illustrates a graph of the voltage over time for the circuit of FIG. 23A.

Figure 24A:
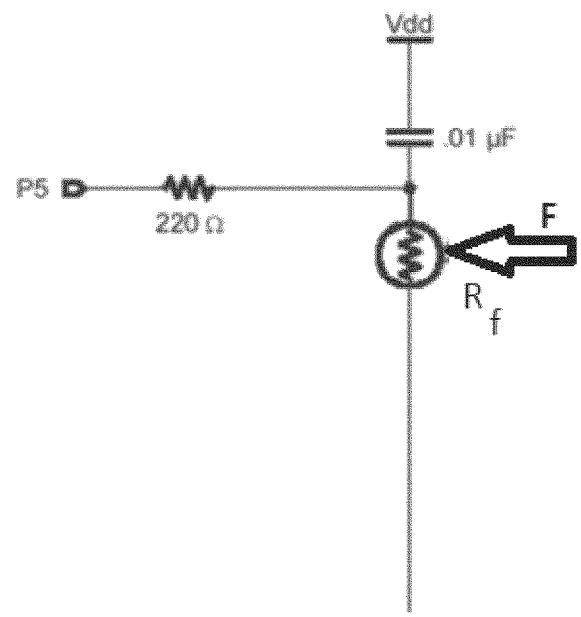
FIG. 24A shows the construction of a Resistance-Capacitor circuitry implemented to determine the resistance of flexi-force sensor. For the given circuit, we measure the charge/discharge time of the capacitor and correlate that to the flexi-force resistance, which in turn in correlated to the amount of force applied on it. This circuit is used to measure the force applied (load force and grasping forces).
Figure 24B:
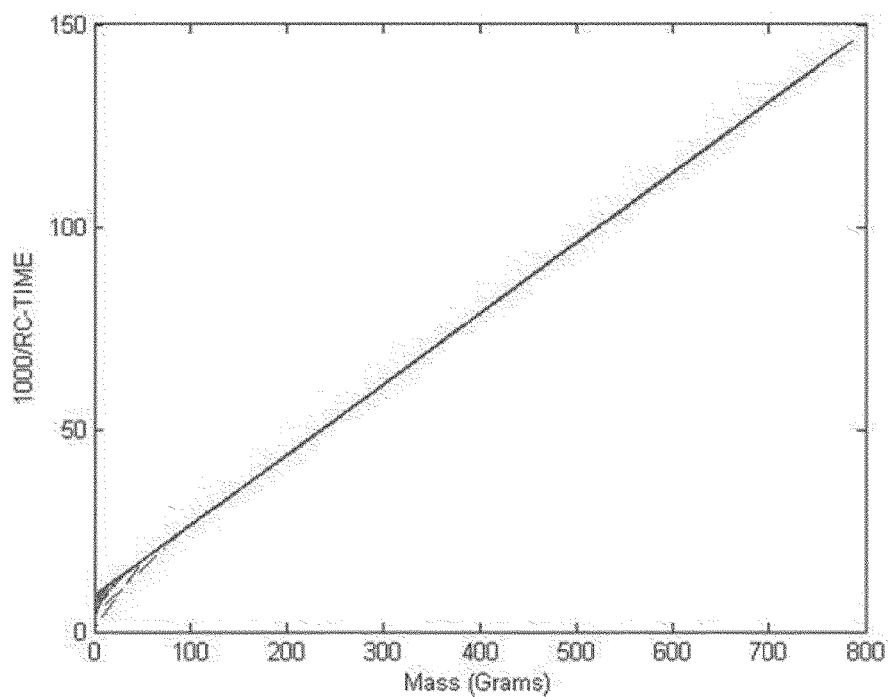
FIG. 24B shows the relationship between the (1000/RC) vs. mass placed on the sensors. From the sensors property of resistance being inversely proportional to the force, it follows that the force is directly proportional to the inverse of the resistance. The above Figure shows this to be the case.
Figure 25A:
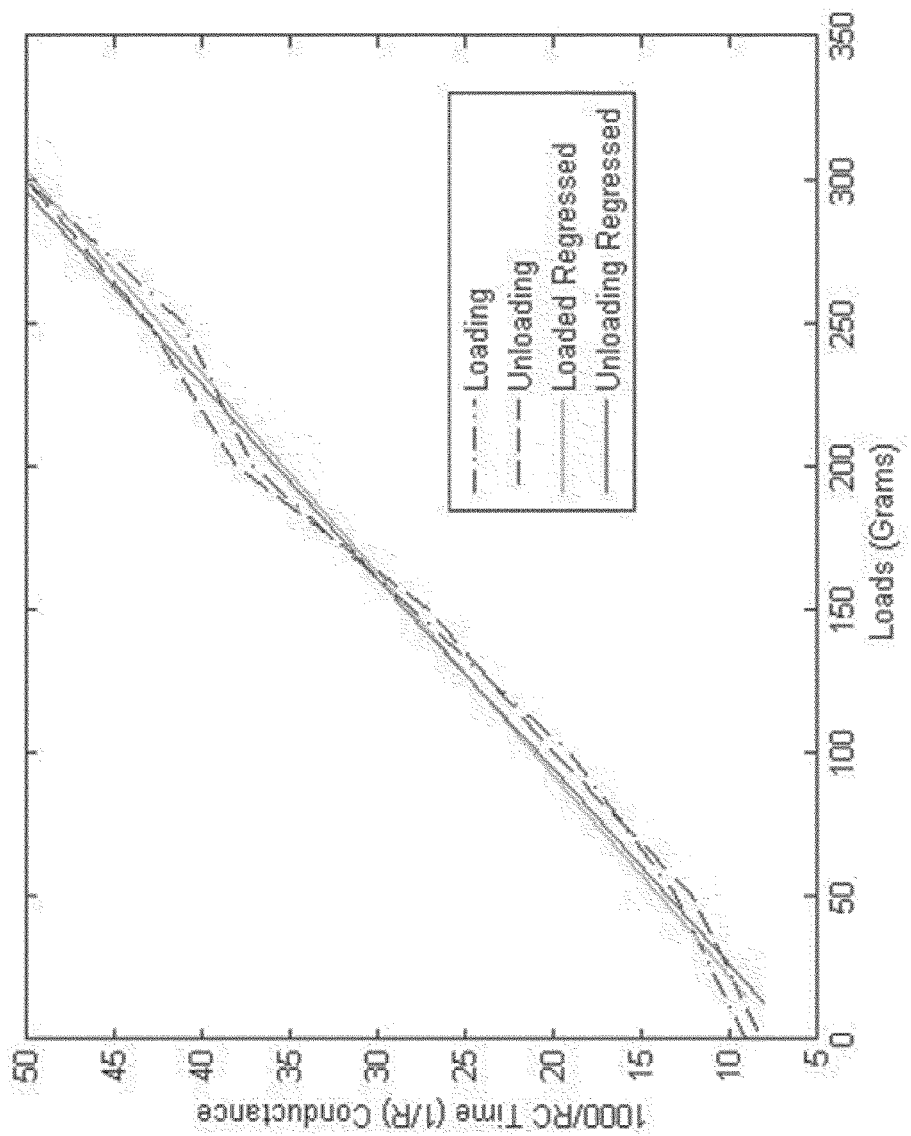
FIG. 25A illustrates Mass (Force) vs. 1000/RC-Time (1/R). The same Resistance-Capacitance circuit was used to determine the loading and unloading characteristics of the device. The loading and unloading data obtained for systematic weights were linearly regressed to obtain a polynomial function to be implemented in code.
Figure 25B:
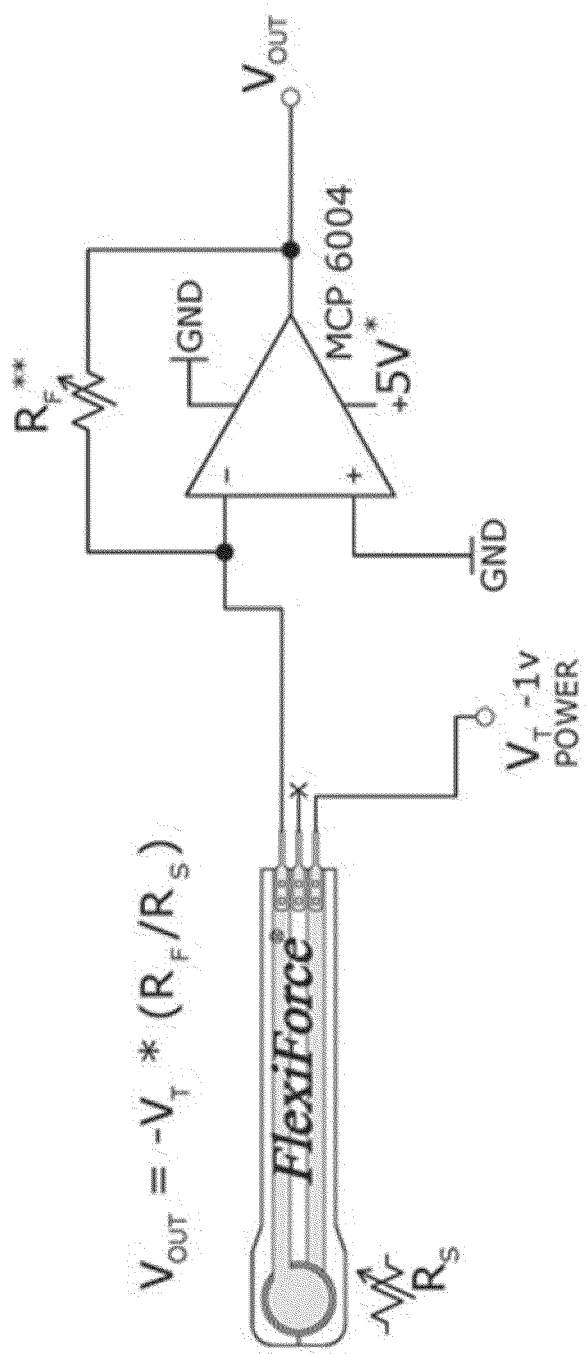
FIG. 25B shows a circuit implementation of Flexi-force sensors with a linear low-power operational amplifier MCP-6004. Upon observation of previous plots in FIG. 24B and FIG. 25A can be observed that the sensors' readings at close to zero are not accurate. The circuit of FIG. 25B was implemented to address this.
Figure 26:
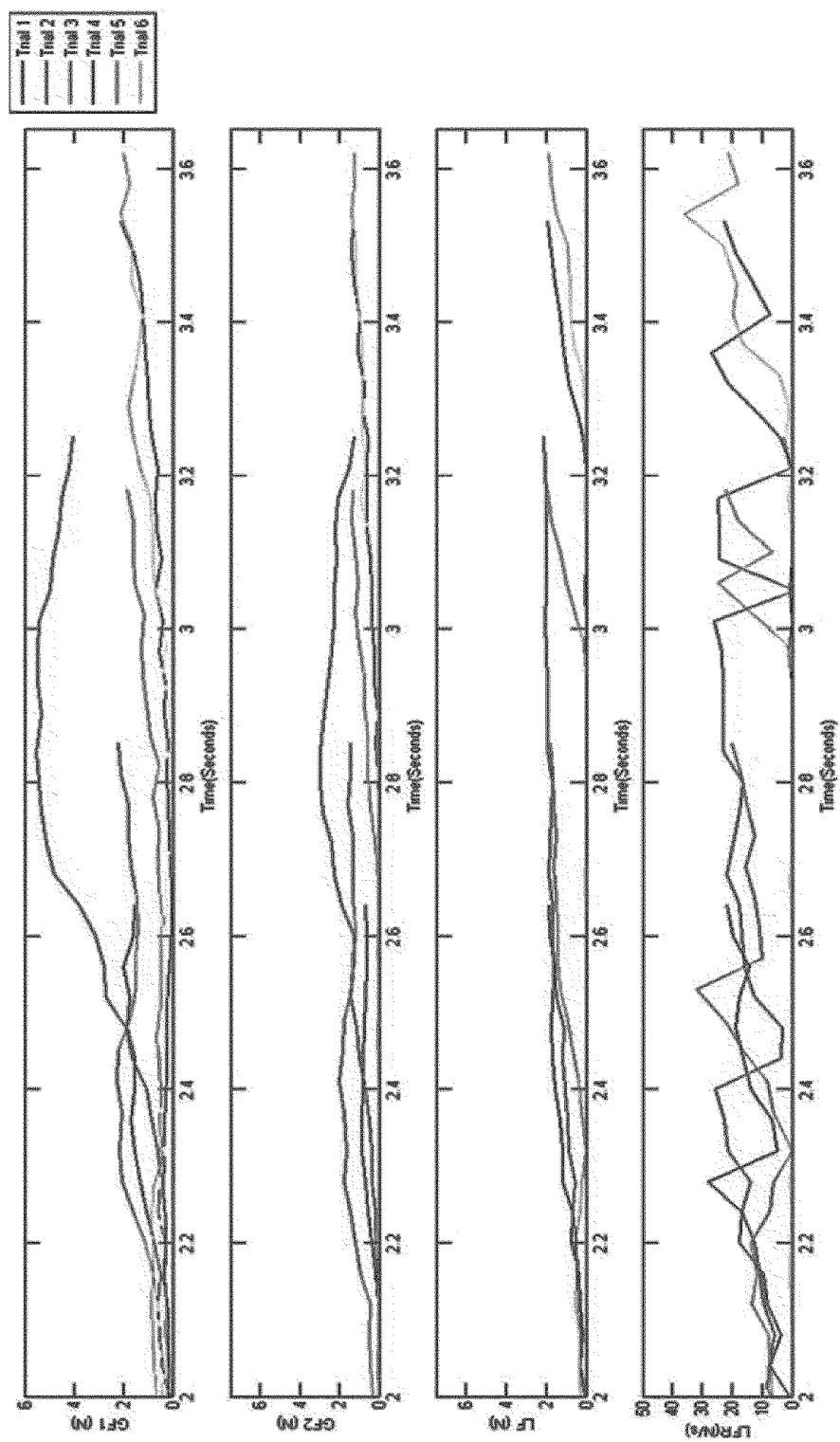
FIG. 26 illustrates results for an experiment with a 250 gram mass and a healthy subject.
Figure 27:
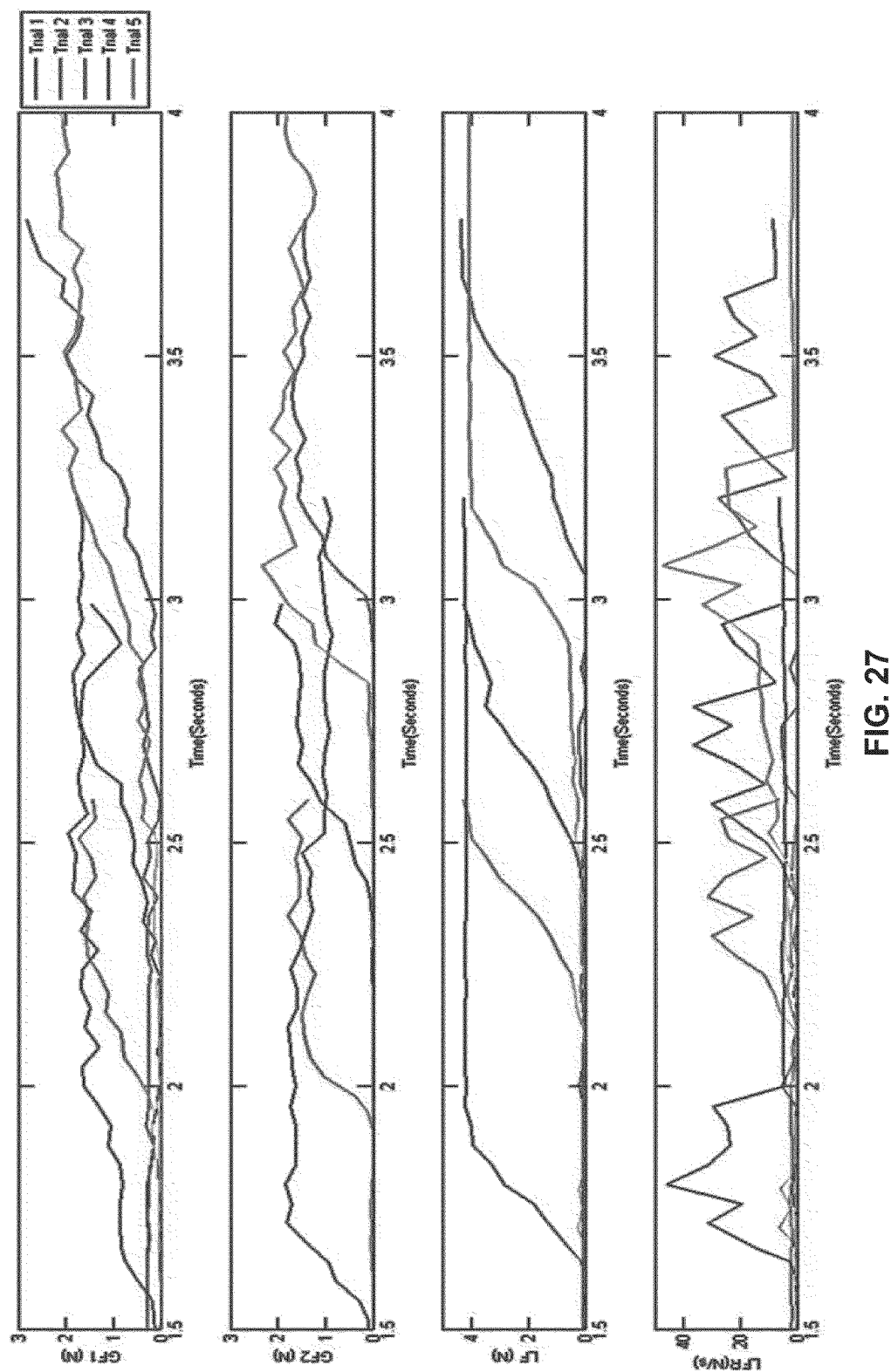
FIG. 27 illustrates results for an experiment with a 500 gram mass and a healthy subject.
Figure 28:
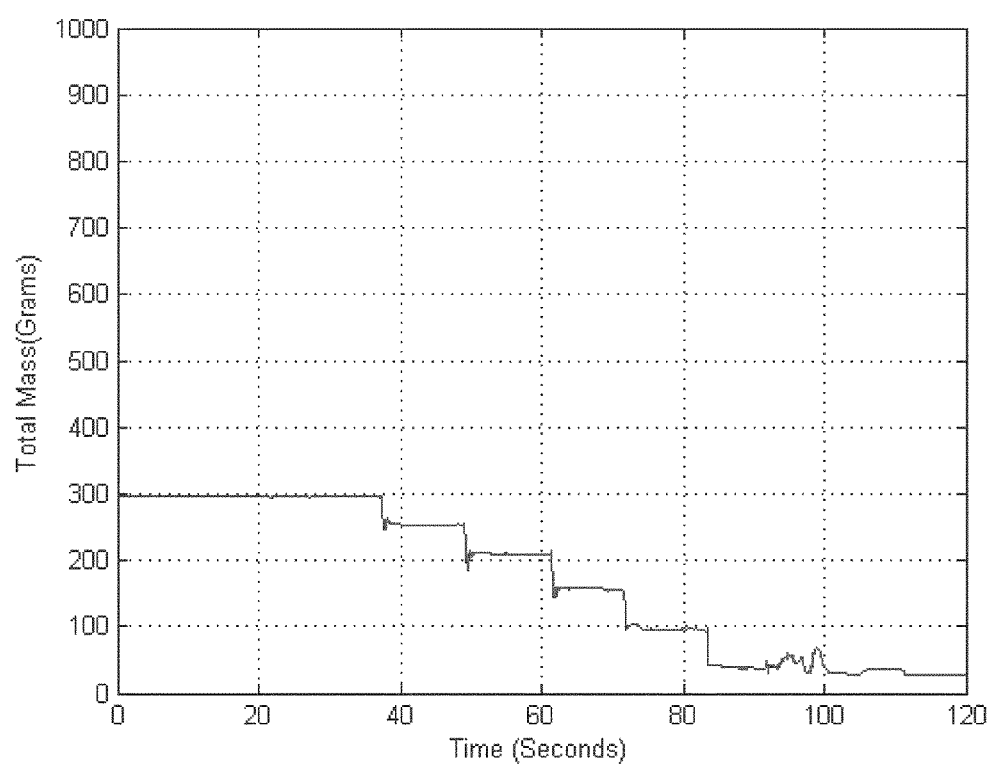
FIG. 28 is a graph of the total mass over time showing the unloading characteristics of the device. This device implements the design of a triangular coaster placed on three flexi-force sensors whose values are summed to obtain the loading and unloading forces.

Moreover, the Resistance Capacitor timing circuit was unable to predict the loads below 30 grams. This results in an error when the subject performs experiment. It is illustrated in the graphs of FIGS. 24B and 25A. The circuit illustrated in FIG. 25B is developed to address performance issues observed in the existing circuit as evidenced in the graphs.

It has been observed that the best alternative was to measure the voltage with no change in current through the sensors 2030. These properties typically are satisfied by operational amplifiers. Tekscan Company recommends utilizing its sensors with MCP6004 Operational-amplifiers. The Analog sensors were powered by an inverted voltage of −4.15V and the output is fed to the inverting Op-amp, the voltage output from the MCP6004 is read using the analog pins in Arduino. Arduino converts the voltage with its inbuilt 10 bit ADC converters. The data plots between the Force-Voltage concurs with the Force-Voltage linear relationship provided by Tekscan. The mathematical expressions relied upon are:

$$F \propto \frac{1}{R_s};$$

where $F$ is force and $R_s$ is resistance of Flexi-force sensor $$V_s = I_s R_s \text{ (From Ohm's Law)}$$

$$I_s = \text{constant} \Rightarrow V_s = R_s;$$

$$V_{out} = -V_s * \left(\frac{R_f}{R_s}\right) \Rightarrow V_{out} \propto F.$$

For

Where $V_s$ the inverting voltage is applied to the flexiforce sensors.

The measured voltage was linearly regressed using Matlab® and a linear regression plot was obtained. The linear regression is encoded into the Arduino Microcontroller to convert the voltages measured into corresponding force measurement. The regression plots are shown below. The Arduino is powered by an ATMega 328 16 MHz microcontroller. This processor calculates the load force rates and grip force rates. The data computed is serially sent to the computer at 115200 baud rate for plotting.

The described experimental setup was capable of providing accurate measurements of 10 grams. The forces observed over a time interval of 35 ms are used to calculate the grip force rates and load force rates. This accounts for a sampling rate of 27 Hz.

As the experiment is designed for rehabilitation purposes, the electronics are designed to restrict the grip force sensors to measure a force up to 9.8 N 1000 grams, whereas the load sensors can measure up to 25 N 2.5 kgs.

The loads measured by summing the load sensors 2032 are linearly regressed with voltage measurement to obtain the force measurements. The accuracy and repeatability of the device 2010 was tested for consecutive loading and unloading experiments. The accuracy and repeatability was found to be under the acceptable limit for the device 2010. In-order to vet the load force applied by the subject, a pulley system was designed to mimic a load applied by the subject. This pulley arrangement facilitates the loading and unloading of the device. One side of the pulley is loaded on the coaster 2051 and weights can be added and removed on the other side of the pulley setup. Static friction could be imminent in this pulley system arrangement. Extra care was taken to perform the experiment repetition to make sure static friction was minimized, so it was neglected in calculations.

For the embodiments of the experiments, the sensors 2030 sample at a rate of 2000 Hz. A general concern is to improve the sampling rate of this device. It was found that the sampling rate of the device is lower, due to the LCD Display command sequence. Where sampling rate is a concern, this can be fixed upon implementation of a gaming platform where the LCD display can be removed. Further, an external display may be utilized by a computer in communication with the device 2010. By removing the LCD display from the device 2010, such an embodiment is expected to have a sampling rate with a minimum value of 100 Hz.

3. Statistical Framework for Game Based Rehabilitator.

The described rehabilitator can be used to facilitate rehabilitation. However, actual use in a clinical setting is greatly enhanced if the proper statistical framework is used to interpret data from the rehabilitator. Making inference regarding a single subject is an important goal in clinical and applied settings in health and behavioral research. In these fields, researchers are interested in assessing whether the individual subject's outcome changes between different conditions such as pre- and post-treatment. Without repeated measures, one can only make a visual judgment regarding the direction and magnitude of the change. Kazdin recommended performing repeated trials under the same condition to reduce the impact of within-subject variability using a repeated measure design such as the ABAB type, where A and B each refer to a different condition. In this case, one can perform a within-subject test evaluating the change using a randomization based test ([14] and [15]). However the classic single subject design and method of analysis does not allow researchers to compare the test subject with a reference population and assess the impact of between subject variability on the decision.

Described herein is one embodiment facilitating making an inference regarding each single subject from a group of test subjects given an available training set of subjects whose statuses are known. Instead of making inference about the average behavior of the test set as a group, the status of test subjects is assessed individually or in small groups and seek to answer questions such as: Does the test subject behave the same as someone in the healthy population as characterized by the subjects in the training set?

Note that in this setup, the sample size of the training set may be very small. The training and the test sets both have repeated measures design, but the number of trials may not be the same. Moreover the experimental conditions for the test may only be a subset of the training set. Described in the below sections is a novel statistical framework for testing the above hypothesis in the context of a single subject experiment, given a small amount of training data. A simple test statistic based on sample mean difference between conditions for the test subject will be compared to a template distribution as a surrogate for the true sampling distribution of the mean difference under the null hypothesis. This template distribution is generated based on Bayesian posterior predictive draws using the training data and the test design.

Described below are a practical solution to the statistical testing problem regarding single-case design, including for use of embodiments of the rehabilitator described herein. In particular, studies and simulation were performed to address an important clinical question: does the test patient behave the same as one from the healthy population? This question cannot be answered using the traditional single subject design in which only the test subject information is used. Borrowing the concept of training and test sets in machine learning, we propose using the Bayesian posterior predictive draws of the training subject data referenced or generated from the test subject design. This yields a template null distribution of a test statistic for the purpose of inference prior to actual testing of new subjects. The performance of this template distribution can also be studied ahead of time. It can be used in a clinical situation and physicians can directly compare the quantity of interest to this distribution to make inference at any desired level. The simulation studies have shown that the proposed test performs satisfactorily when compared with its counterpart test in which the true sampling distribution of the test statistics is given or known. Moreover, an estimate of the error rate and its confidence interval is provided given a single training data set, which can further inform physicians about the reliability of the test results based on the given template/experimental design.

Compared to the traditional single-subject design approaches, the proposed method has the following advantages:

1. It can be easily adapted to test a range of quantities of interest. Described below are examples with a simple mean difference based statistic, but physicians may be interested in using the between trial variability as a measure of performance, for example. Using the algorithm for deriving template distribution set forth below, the template distribution of the between-trial variability can be conveniently produced based on the between-trial variability of $\check{Y}_{ijt}$.
2. Embodiments of the proposed test are based on a small sample of training subject data. In general, it is expected that the training subject data to be a random sample and the experiment is done in a well-defined laboratory setting. Albeit a small sample size (for example N=10), a more complex design that better informs the between-subject and within-subject variability can be used. Examples herein use a training subject design with 10 weights and more trial replications. In contrast, the test subject design is allowed to be simpler so that it is feasible for patients in a clinical setting.
3. Another advantage of the proposed method is that it can be used to inform single-subject design. Based on the derived error rates associated with different test designs, researchers and clinicians can determine ahead of time, an experimental design for the test subjects with conditions and repeats that optimizes the error rates and power among all the feasible options.
4. Lastly, in a tele-medicine situation, when the physicians are able to download a template distribution provided from the research labs and upload clinical data to the lab, the proposed method will most effectively allow the outcomes in the basic research laboratory to be quickly applied to clinical setup, and in addition allows rapid integration of newly collected clinical data for the purpose of basic research.

The analytic technique provides a crucial component to make sense of the data gathered by the rehabilitator. Specifically, how the algorithm will be used by the rehabilitator is illustrated in the following non-limiting case examples. The rehabilitator was initially designed to train and assess the ability to grasp objects of various weights, textures and shapes. Below, examples illustrate a how the algorithm can be used to assess the use of appropriate grasping forces when the weight of the objects is changed. All the applications can be applied directly to texture and shape variations as well. In other words, the algorithm will facilitate a single-subject experiment which will provide not only the raw data and averages, but an estimate of the error rate, and false-positive and false-negative rate to facilitate decision making regarding questions such as:

Is the patient improving or not
Should the treatment continue or be changed
What is the rate of improvement
What is the prognosis for further improvement
Case 1 a (for Weight Sensing Assessment):

The rehabilitator gathers the force data in several dimensions and over a time period, and preprocesses the data to provide a single measure (the peak load force rate, PLFR) which is a measure of learning or the ability to predict the weight of the object to be manipulated even before it is lifted. This data will be collected by the mechatronic device patented earlier this year. Due to inter-trial variability, the patients need to perform multiple trials in order to reliably interpret the data collected. This proposed algorithm will produce a measure that takes into account the between-trial variability under different repeated designs Case 1b (for Weight Sensing Assessment):

given a reliable estimation of the PLFR, the clinician will be notified of a single decision based on a precalculated template regarding whether the patient being tested is learning in a HEALTHY manner. The algorithm is based on a rigorous statistical process.

Case 1c (for Weight Sensing Assessment):

For the decision made in 1 b, this algorithm will also provide a rigorous assessment on the accuracy of the decision, i.e. if the patient is deemed to be healthy, what is the false negative rate associated with this decision? If the patient is deemed to be unhealthy, what is the false positive rate associated with this decision?

Case 1 d (for Weight Sensing Assessment):

The single subject design has low power because we only have one subject. This algorithm will provide a post-hoc power analysis to inform what would be a more optimal assessment design to increase the power (and reduce the error in decision) for the single subject.

Case 1 e (for Weight Sensing Assessment):

The algorithm will allow customization to further improve the validity of such tests. Some of the key parameters (such as different levels of between trial variability) will be allowed to be imported by the clinicians to fit the specific situation of the single subject.

Case 1f (for Weight Sensing Assessment):

The algorithm can also perform assessments of other variables per the clinician's request. For example, the learning curve between trials, the variability between trials, etc.

Case 1 g (for Weight Sensing Assessment):

The data intensive computation will be done behind the scene, ahead of time. The specific information the rehabilitator needs to conduct all the aforementioned functions can be implemented using a very simple and fast set of algorithms installed on a computer or built on a small computer chip attached to the rehabilitator as described in the previous patent for the mechatronic device. The software can be downloaded and updated conveniently via the internet. The data/results produced by the rehabilitator can also be uploaded via the internet to for algorithm updating.

In one embodiment, the algorithm for use in the statistic framework has the following components: 1. A precalculated template: the template is computed behind the scene using laboratory collected healthy subject data. The calculation of this template will involve a new algorithm that involves a novel application and revision of some known statistical procedures. 2. A built-in algorithm in the rehabilitator: this algorithm will calculate a reliable measure of the PLFR, and use the template to make assessments regarding the status of the patient, and calculate the error rate associated with the decision. This decision making process is based on a new algorithm.

The rehabilitator described in various embodiments above may have a computer chip to facilitate the data collection, processing and communication described herein. For example, in one embodiment a small computer chip can be installed on the rehabilitator, or the algorithm can be directly installed on a computer that is linked to the rehabilitator.

a. Precision Grasp as a Model Task

In post stroke rehabilitation, precision grasp is an important task as it is closely related to patients daily activities. Precision grasp depends on anticipatory control, an ability to predict the optimal force when lifting a familiar object such as a cup of coffee. In healthy individuals, it has been found that after just one or two practice lifts the rate of change of load force is faster for a heavier object than for a lighter object ([8] [9]). More specifically, Lu et. al. ([19]) show that after one practice trial, the Peak Load Force Rate (PLFR) increases proportionally as the weight of the object being lifted increases.

However, anticipatory control is often impaired among patients with brain injury due to stroke. Restoring and assessing the ability of anticipatory control is an important goal in post-stroke rehabilitation. Using a rehabilitator device, such as described above, PLFR can be readily measured during a designed grasping and lifting task involving different weights, and it can be used as a convenient clinical measure for physicians to assess whether each patient is capable of executing anticipatory control during different stages of the rehabilitation process.

Figure 30:
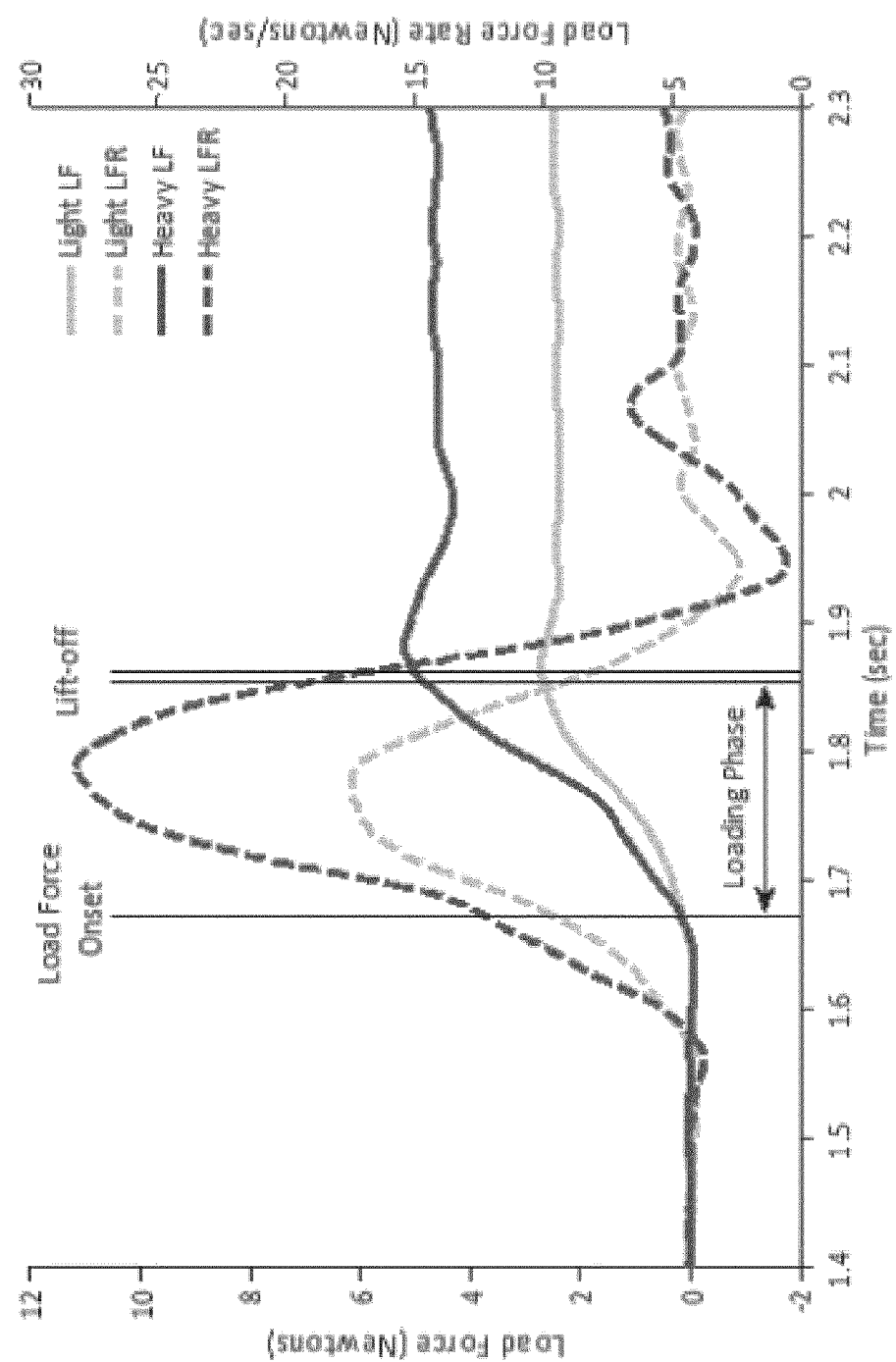
FIG. 30 shows rate of change in load force when lifting objects of different weights: The load force profiles of a subject grasping the grip device of two different weights with precision grip and lifting it with the dominant hand are shown in solid line. The derived force rate curves are shown in dashed line. Black indicates heavier object and grey indicates lighter objects. The peak Load Force Rate is defined as the highest point in the force rate profile.

According to Lu et. al. ([19]), the logarithm of peak Load Force Rate increases linearly in the object's weight among healthy subjects (see an illustration in FIG. 30). Mathematically, this can be expressed as:

$$\log(PLFR_i) = \alpha_i + \beta WEIGHT_{it} + E_{it}, \quad (1)$$

where individual i is lifting weight $WEIGHT_{it}$ on trial t, and $E_{it}$ is idiosyncratic error. The terms $\alpha_i$ and $\beta$ reflect individual-level baseline force and population-level (common) effects for different weights, respectively. Based on a sample of 10 healthy subjects, the scaling factor is found to be 1.4 Newton/ms per 1000 grams weight increase. Moreover, although individual subjects may have different PLFR when lifting, namely different speed in loading force to lift, the manner in which PLFR scales up as a function of weight is fairly constant. In other words, in the above linear model, each subject could be found to have his/her own intercept ($\alpha_i$), but they all share a common slope (the scaling factor $\beta$).

Under the framework of model (1), assessment of anticipatory control can then be formulated into the following hypothesis testing problem.

H0: Patient has healthy anticipatory control The PLFR of the test subject increases as the weight of the object increases the same way as in the healthy population. $\beta_{test} = \beta_{pop}$.

Ha: Patient does not have healthy anticipatory control The test subject fails to adjust the loading force rate due to weight changes, hence PLFR does not increase the same way as in the healthy population, $\beta_{test} < \beta_{pop}$ To test this hypothesis, one needs to estimate the benchmark value for the scaling factor among healthy population, $\beta_{pop}$, and the scaling factor for the test subject, $\beta_{test}$. Moreover, since PLFR is a behavioral measure, there is substantial trial to trial variability when the same subject lifting the same weights for multiple trials, and there is substantial between subject variability due to individual behavioral idiosyncrasy ([19]). Hence a good statistical test should take into account the uncertainty introduced by both between and within subject variability.

b. Data and Existing Approaches i. The Data

First the data that is typically seen in the grip force example is described. A small training data set of 10 healthy subjects, lifting 10 weights ranging 250 to 700 grams, 50 grams apart was used. At each weight, each subject lifts the object for 7 trials while the first trial is a learning trial where the new weight is presented in a random order and unknown to the subject. After first trial, healthy subjects are capable of applying anticipatory control [19] hence a total of 6 learned trials. While small in the number of subjects, this is reasonably large in the number of conditions and replications, allowing for precise estimation of underlying physiological features and their variation.

The test set consists of some stroke patients. Due to time and physical limitations, each test subject only lifts two to three different weights; referred to as scenarios one and two, respectively. For each weight, the test subject performs one practice lift in order to learn the weight of the object, then repeats for five trials.

ii. A Natural Estimator

In a clinical setup, the most straight-forward way to estimate the scaling factor of the test subject is to simply take the difference in the peak load force rate measured at different weights, averaged over multiple trials. If the subject only lifts two weights, a naive sample mean based estimator of the scaling factor is, $$\bar{\beta}_i = \frac{\sum_{t=1}^{T}(y_{i2t} - y_{i1t})}{T(w_2 - w_1)}$$

where $y_{i1t}$ is the PLFR measure for subject i lifting weight one of $w_1$ grams at the tth trial (t=1, ..., T), and $y_{i2t}$ is the corresponding measure when subject i lifting weight two of $w_2$ grams at the tth trial.

Sometimes, the test subject can be instructed to lift three weights (or more) of equal distance, in which case, the PLFR can be estimated by averaging of the differences in PLFR between adjacent pair of weight then divided by the weight difference per pair. Putting it in a general formula assuming J weights with equal distance $d_w = w_2 - w_1$, $$\bar{\beta}_i = \frac{\sum_{j=2}^{J}\sum_{t=1}^{T}(y_{ijt} - y_{i(j-1)t})}{(J-1)Td_w}$$

Following [19], the scaling factor for healthy population can be estimated using a linear mixed effect model based on the 10 subjects, and they report an estimated benchmark value $\beta_{pop}$=1.4 N/ms per kilogram of weight increase. They further prescribe a 95% one-sided confidence interval based on the standard error of this estimator: [1.27, ∞). A naive approach is to compare the scaling factor for the test subject $\hat{\beta}_i$ with the estimated benchmark value along with this confidence interval. If $\hat{\beta}_i$ falls outside the prescribed the confidence interval, the physician can be instructed to reject the alternative hypothesis.

Albeit it simple, this approach is not ideal as 1) the prescribed confidence interval is too narrow because it is for the mean scaling factor across a healthy population, and it doesn't take into account of the impact of between subject variability for the purpose of comparison; 2) the within subject (between trial) variability is not incorporated.

iii. Hierarchical Linear Model Via MLE

An applied statistician might take a modelling approach to compare the scaling factor between the training subjects and the test subject. Since each subject is asked to lift the object for multiple trials and under different weights, the expected outcomes will be clustered/correlated within the same subject and the same weight. As Lu ([19]) pointed out, a linear hierarchical model can be used to model this type of data ([12]).

Since the training data and the test subject use different experimental designs, and a different scaling factor β is expected, the model for each group was outlined separately using a modified notation. The following two level linear hierarchical models, substituting Y for log(P F RL) and W for WEIGHT, characterize how the observations are generated:

$$\begin{cases} Y_{ijt} = \alpha_i + \beta^{pop}W_{ij} + u_{ij} + \epsilon_{ijt}, & \text{model for training data} \quad (3.1) \\ Y_{i'j't'} = \alpha_{i'} + \beta^{test}W_{i'j'} + u_{i'j'} + \epsilon_{i'j't'}, & \text{model for test subject} \quad (3.2) \end{cases}$$

for subjects i in the normal or training population, i=1, ..., N train, and subjects $i_t$ in the test or new population where $i_t$=1 in the single-subject design. Subscripts t and t indicate the trial number for each $^E$group, t=1, ..., T and $t_i$=1, ..., $T_i$. $W_{ij}$ and $W_{iiji}$ specify the weight of the objects being lifted. $u_{ij}$ and $u_{iiji}$ specify the subject-weight specific effects and they are assumed to follow N(0, $\sigma_2$). The error terms $E_{ijt}$ and $E_{iijit}$ are assumed to be independently distributed N(0, $\sigma_2$). Note that common variances are assumed for many of the model components, to borrow strength from the information gained from the training subjects, but to the extent that test-subject-specific variances wish to be and can be identified, these assumptions can be relaxed.

Instead of testing hypothesis $H_0$: $\beta_{pop} = \beta_{test}$, an equivalent hypothesis $H_0$: $\delta = \beta_{pop} + \beta_{test} = 0$ is considered. The quantity δ can be estimated under the linear hierarchical framework by combining the training data and the test subject, specifying an indicator variable, $NEWSUBJ_i$, set to 1 if subject i is in the new population and set to 0 otherwise. Then, a joint model such as this is fit:

$$Y_{ijt} = \alpha_i + \beta^{pop}W_{ijt} + \delta W_{ijt} \times NEWSUBJ_i + \epsilon_{ijt} \quad (4)$$

The above model can be fit using standard statistical software packages such as SPSS, SAS, Stata or the nlme package in R (among others) under the Maximum Likelihood Estimation framework. Fitting this model will produce point estimates of $\beta_{pop}$ and δ as well as their standard errors. One can construct a Wald-type statistic (point estimator/ standard error) to test whether the difference in scaling factor δ is significantly different from 0 by comparing it with a t distribution. However, since the Wald test is a large sample based result, when there is only one test subject, it is not appropriate to use the t distribution as the null distribution for the test. As an alternative, permutation based tests are often used for finite samples, but in this example, there are a total of 11 subjects, so the permutation based p-value cannot be smaller than 1/11, which implies the power of the test will be zero if one tries to control the type I error to be at 5%.

Other issues with MLE approach is that the commonly used software packages tend to be based on strict assumptions about the error structure, such as the within-subject variation is the same for the training set (healthy subjects) and the test subject (typically patients).

iv. Bayesian Hierarchical Linear Model

An alternative to the Maximum Likelihood Estimation is a Bayesian hierarchical model fitting approach [5]. To fit a Bayesian model, one needs to first specify a set of prior distributions (and sometimes hyper-prior distributions) for the parameters of interest. The choice of prior distributions is important as it can have substantial impact on the model.

Since the specification and estimation of Bayesian model require certain level of statistical knowledge, it is less available to practitioners.

To fit (4) under the Bayesian paradigm, one would specify the following prior and hyper-prior distributions for the training data, $$p(\beta^{pop}, \sigma_{\epsilon_1}^2) \sim \frac{1}{\sigma_{\epsilon_1}^2}$$

$$p(\alpha_i) \sim N(0, \sigma_{\alpha_1}^2)$$

$$\sigma_{\alpha_1}^2 \sim Inv-Gamma(\eta_1, v_1)$$

and for the test subject $$p(\beta^{test}, \sigma_{\epsilon_2}^2) \sim \frac{1}{\sigma_{\epsilon_2}^2}$$

$$p(\alpha_i) \sim N(0, \sigma_{\alpha_2}^2)$$

$$\sigma_{\alpha_2}^2 \sim Inv-Gamma(\eta_2, v_2)$$

Notice here that the Bayesian model allows us to explicitly specify the variance components differently for the training data and the test subject. On the other hand, this setup also allows one to borrow strength and estimate the variance components jointly by forcing $\sigma_{\alpha_1}^2 = \sigma_{\alpha_2}^2$ and $\sigma_{\epsilon_1}^2 \sigma_{\epsilon_2}^2$.

In one embodiment, non-informative priors were applied to avoid the impact of prior influence on model estimation [5][2], with the exception of the subject-specific intercept variance. Since there are only 10 training subjects and 1 test subject, an informative prior, the inverse gamma distribution, was applied on the variance of $\alpha_i$. This prior (Inv-Gamma($\eta$, v)) is determined by two parameters $\eta$ and v, corresponding to a prior mean variance value v/($\eta$−1). The choices for v, $\eta$, correspond closely to the MLE estimate of the variance.

The Bayesian approach then estimates the parameters via posterior simulation. Let $\Theta = (\beta_{pop}, \beta_{new}, \sigma_2, \sigma_2, \sigma_2)$, then the posterior distribution can be derived using Bayes formula, $$p(\Theta | Y^{train}, Y^{test}, W^{train}, W^{test}) = \frac{p(Y^{train}, Y^{test} | \Theta, W^*)p_0(\Theta)}{\int p(Y^{train}, Y^{test} | \Theta, W^*)p_0(\Theta)d\Theta}$$

$$\propto p(Y^{train}, Y^{test} | \Theta, W^*)p_0(\Theta)$$

where $W^* = \{W_{train}, W_{test}\}$ and $p_0(\Theta)$ is the prior distribution of the parameters. When the closed-form of the posterior distribution is not available, it can be approximated using Monte-Carlo simulations and used for inference.

For this example, with a simple reparameterization, $\beta_{test} = \beta_{pop} - \delta$, the posterior distribution of $p(\delta | Y_{train}, Y_{test})$ can be generated. Unlike the MLE approach, in which a single point estimator $\delta$ is produced for the quantity of interest, the posterior distribution of $\delta$ is the basis of Bayesian inference. For example the maximum a posteriori probability (MAP) value is the $\delta$ value corresponding to the peak of the posterior distribution and can be viewed as a Bayesian version of the point estimator, the posterior standard deviation is a measure of the variability in $\delta$ (there is no sampling distribution of an estimator; instead, there is a posterior for the corresponding parameter).

However, the Bayesian hypothesis testing does not come naturally due to the fundamental difference in problem formulation—the Bayesian approach posits that all parameters are random variables and follow a distribution, which is estimated by the posterior distribution, while the Neyman-Pearson type of hypotheses typically focus on a single parameter value. [13] proposed posterior p-value, the Bayesian counterpart of the classical p-value by simulating the joint posterior distribution of replicate data and the (nuisance) parameters, both conditional on the null hypothesis and calculating the tail area probability of a "test statistic" using this distribution. However, the posterior p-value has been criticized for its tendency to center around 0.5 for hierarchical model [5, 4]. Instead, a shorthand way of evaluating the posterior probability of $\delta < 0$ is considered. Namely, for a test at level 5%, if p($\delta < 0 | Y$ train, Y test) < 0.05, then the null hypothesis is rejected. In other words, in this instance, there is sufficient evidence (95% of the posterior mass) to support $\delta > 0$, or deviation from the training data.

c. Approach to Single-Subject Design Analysis

Unlike directly comparing the naive estimator in equation 2 with a predetermined benchmark value and make a visual judgement about the status of the test subject, the use of Maximum Likelihood and Bayesian modeling allow us to compare the test subject with the training data set taking into account the within-subject and between-subject variability, and statistical tests are available to assist decisions under these modelling frameworks. However these approaches are not practical in the clinical setting. In order to make an inference regarding a new subject, one needs to refit the entire multilevel model, which is time consuming and not user-friendly in the clinical setting. Without proper training in statistics, these methods are practically unavailable to the clinicians. Moreover since most of the statistical parametric modelling approach depends on a large sample, the behavior of the aforementioned methods in hypothesis testing regarding a single subject is unknown. The error rates such as false positive and false negative rates associated with the decisions can be off target.

To address these concerns, one embodiment uses a novel approach that will allow clinicians without any formal statistical training to make an informed decision about the test subject's status as compared with reference subjects in the training data.

One embodiments starts with the naive estimator $\bar{\beta}_{new}$ based on equation 2, which is available. The Bayesian approach handles the non-asymptotic setting more elegantly, but is inherently more difficult to fit without specialized knowledge of statistical programming languages such as STAN, BUGS or JAGS in the clinical setting. The goal is to provide the clinician with a template distribution of the possible values that are expected to be observed given the weight design and the number of repeated measures used by the test subject. This template distribution is to be developed in a laboratory where the scientists and statisticians collaborate to design experiments and collect data based on a carefully controlled set of training subjects, for example, a random sample of healthy subjects.

Based on the template distribution, the clinician can easily test the hypotheses such as H0: Patient has healthy anticipatory control $\beta_{new} = \beta_{pop}$.
Ha: Patient does not have healthy anticipatory control $\beta_{new} < \beta_{pop}$ The probability of observing any values $\beta_{new}$ as extreme as the naive estimate $\bar{\beta}_{new}$ had the test subject behaved the same way as the reference population can be easily generated using the template distribution. This probability has the interpretation of a classic p-value in a statistical inference problem (P(observation as extreme|model) under the null). The clinician can choose a desired level of the test, say 0.05 and reject the null hypothesis whenever the p-value is less than 0.05. An equivalent alternative is to compare the naïve estimate $\bar{\beta}_{new}$ directly with the critical value $C_{0.05}(\bar{\beta}_{new})$ derived from the template distribution. If $\bar{\beta}_{new} < C_{0.05}(\bar{\beta}_{new})$ then reject the null hypothesis.

Moreover, since the template distribution is derived in a laboratory setup, the performance of such decisions can be evaluated ahead of time. Along with a convenient test, the expected error rates associated with the decision will also be reported.

i. The Algorithm for Deriving the Template Distribution

To derive this template distribution, a feature of Bayesian modeling is exploited, which is that posterior predictions are easily computed using any combination of model parameters. Crucially, this allows one to vary the design between training and test subjects and propagates parameter uncertainty into the predictions, providing a natural framework for statistical inference that does not rely on asymptotic theory. The steps for deriving the template distribution include:

1. A Bayesian hierarchical model is fit using the training data set alone to obtain the posterior distribution of the parameters. For model 3.1 (Hierarchical Linear Model), these parameters are $\Theta = \{\alpha, \beta^{pop}, \sigma_\alpha^2, \sigma_u^2, \sigma_\epsilon^2\}$, for which it is labeled the posterior $h(\Theta) = p(\Theta|Y^{train})$.

2. Given a new design $W_{new}$, it is assumed, under the null, that all parameters $\Theta$ in model 3.2 (a hierarchical linear model) are the same. A set of posterior predictive outcomes $\tilde{y} \sim MVN(\mu_{new}, \Omega_{new})$ are generated, where for this model $\mu_{new} = a + \beta_{pop} W_{new}$ and $\Omega_{new}$ has compound symmetry structure induced by the random effects for intercept and trials. Specifically, $$\{\Omega^{new}\}_{ijt,i'j't'} = \begin{cases} 0 & \text{if } i \neq i' \\ \sigma_\alpha^2 & \text{if } i = i', j \neq j' \\ \sigma_\alpha^2 + \sigma_u^2 & \text{if } i = i', j = j', t \neq t' \\ \sigma_\alpha^2 + \sigma_u^2 + \sigma_\epsilon^2 & \text{if } i = i', j = j', t = t' \end{cases}$$

This posterior, $p(\tilde{y}|\Theta, W_{new})$ can be viewed as the distribution of the future outcomes that would be observed, were the new design applied to subjects from the training sample. By generating these pseudo-outcomes in a Bayesian framework, the model uncertainty is propagated from $h(\Theta)$ to the predictions, $\tilde{y}$, representing our current understanding of the physiological process, and this can be updated should more training subjects become available.

1. In order to construct the template (reference) distribution, a large sample is needed of pseudo-subjects drawn from $p(\tilde{y}|\Theta, W_{new})$. For any new subject i, take $\tilde{y}$ and compute $\bar{\beta}$ using equation (2). This is the natural single-number (non-parametric) summary statistic one would compute for a new subject. The density of $\bar{\beta}$ over a large number of such pseudo-subjects is an approximation to the distribution for a randomly drawn new subject under the null hypothesis. Given a predetermined false positive rate (FPR), say 5%, the critical value for rejecting the null hypothesis can be obtained empirically.

2. Recall that $\beta_{new} = \beta_{pop} + \delta$. As in step 1, the posterior predictive draws of $\tilde{y}$ under a specific alternative value of $\delta$, call it $\delta_{alt}$, can be obtained by a location shift of the posterior predictive distribution of $\tilde{y}$ by $\delta_{alt}$, again, due to the linearity and normality of the models examined. Then, following steps 2 and 3, distributions of $\bar{\beta}_{alt}$ are obtained under hypothesized alternative values of $\delta_{alt}$. These distributions can be used to assess the false negative rate (FNR) or power of the decisions made regarding to the hypothesis.

d. Simulation Studies

A set of simulations were conducted to assess the performance of the proposed method. The method is applied to the hypothesis testing problem of whether a (new) test subject has healthy anticipatory control. This test is based on the naïve estimator $\bar{\beta}_{new}$ and our Bayesian model-based template distribution. As comparison, the performance of a Bayesian hierarchical model and the Wald test for the MLE estimator $\delta$ in a linear mixed effects model are also tested.

i. Setup

For the basic simulation setup, multiple samples of training data and test subjects will be simulated according to the following data generating process:

Training data The training data contains 10 subjects simulated from model (3.1), with the scaling parameter $\beta_{pop} = 1.4$. The other parameter values are set as follows, $a = 2.8$, and $\sigma\alpha1 = 0.3$, $\sigma u1 = 0.1$ and $\alpha E = 0.2$. This set of parameters are assumed to be the population parameters of the healthy subjects.

The design matrix for the training data assumes that each subject lifts 10 weights, ranging from 250 grams to 750 grams, 50 grams apart. The subjects lift each weight for 6 trials (after an initial practice trial that is discarded).

Test subject The test subject is also simulated following model (3.2) with the same parameter values as the training data set except for $\beta new$. A range of scaling factors $\beta new$ from 1.4 to 0.1 will be used, covering both the null and alternative parameter space. The design matrix used for the test subject is different from that used in the training set. Since the test subjects will typically be patients, a less involved weight design and fewer repeated trials will be used. For test subjects, the number of trials after practice is set to 5. Two weight design scenarios 1 and 2, defined respectively as:

Each subject lifts only two weights at 250 grams and 500 grams

Each subject lifts three weights, at 250, 500 and 750 grams

When the test subject is simulated under $\beta new = \beta pop = 1.4$, it corresponds to the null hypothesis. When the test subject is simulated under $\beta new < 1.4$, it corresponds to a case within the alternative hypothesis parameter space. The purpose of the simulation studies is to compare the performance of different methods in terms of false positive rate and false negative rate. To estimate false positive rate and false negative rate, a large number of replicates of the training and the test sets are generated as necessary.

For each replicate of a simulated data set, consider four different ways of estimating the parameters of interest and testing the null and alternative hypotheses.

Test A: Naive Estimator $\bar{\beta}$ and its Sampling Distribution

For a single simulated test subject, $\bar{\beta}new$ was calculated using (2). This is denoted as estimator $\bar{\beta}new$ when the test subject is simulated under the null hypothesis (when $\bar{\beta}new = 1.4$). The distribution of 1000 samples of $\bar{\beta}_0^{new_s}$ approximates the sampling distribution of denoted by Dist (A)·$\bar{\beta}new$ under the null hypothesis, denoted by Dist(A).

A decision rule is proposed using Dist(A): for a one-sided test at level $\alpha$, the rejection region is $D\alpha, A = \{\bar{\beta}:$ $\bar{\beta} < C\alpha, \text{Dist}(A)\}$, where $C\alpha, \text{Dist}(A)$ is the $\alpha$th percentile value of $\text{Dist}(A)$. By directly by comparing a new subject's naive estimator $\bar{\beta}$ with this rejection region, a decision can be made regarding a single test subject.

When the hypothetical test subject is simulated using a range of values $\beta\text{new} = \beta\text{pop} - \delta$, where $\delta = (0.1, 0.2, \ldots, 1.3)$, it forms the alternative hypothesis space. For each value of $\beta\text{new} < 1.4$ so derived, one estimate the false negative rate by summarizing test results across 1000 copies of new test subjects. Note that the false positive rate for this test is a by construction.

To construct this test, a model for the data generating process is used, which us assumed as a close approximation to what would be observed in a large population of normals. Since the decision rule is based on the sampling distribution of the test statistic $\bar{\beta}\text{new}$ under the null, and the nature of this test is non-parametric, one would use the error rates derived based on this test as the "gold standard" for comparison purposes.

Test B: The Estimator $\hat{\delta}$ and Bayesian-Based Template Distributions

Following the method outlined above, Using the R Bayesian package rstan, a first fit model (3.1) is used to train data with non-informative priors on the hyperparameters, except for $\sigma^2$. The prior values for the hyperparameters are set to $\eta = 5$, $v = 1$. Three Markov Chain Monte Carlo (MCMC) chains were run, each of 2000 draws. The first 1000 draws of each chain are burn-in and are discarded. Based on the Bayesian fit, 3000 posterior predictive draws of $\tilde{y}$ were generated using the test subject design. It is important to note here that this approach is "borrowing" the design used in a future observation as a template, but it does not actually use any real future observations in the construction of the reference distribution (as opposed to the Bayesian hierarchical modeling method, which does estimate a $\delta$ from the test data). The template distributions are derived following steps 1-4 in the proposed algorithm described above. In particular, the template distribution is denoted under the null hypothesis $\text{Dist}(B)$.

Note that each set of training data generates a complete template null. This generative process is repeated across different training data to understand the variability inherent in the Bayesian analysis. In practice, a single template null will be used.

A decision rule is proposed using $\text{Dist}(B)$: for a one-sided test at level $\alpha$, the rejection region is $D\alpha, B = \{\bar{\beta}: \bar{\beta} < C\alpha, \text{Dist}(B)\}$, where $C\alpha, \text{Dist}(B)$ is the $\alpha$th percentile value of $\text{Dist}(B)$. By directly by comparing the naive estimator $\bar{\beta}$ with this rejection region, decision can be made regarding a single test subject. Similarly, the error rates associated with this test can be summarized when using different true $\beta\text{new}$ values for the alternative.

This is also the method proposed for the physicians to use in the clinical set-up. In this case, the empirical error rates are not available, but they can be calculated based on examining the overlapping areas between the template distributions under the null and under a specific alternative parameter value. This slightly different simulation design is called $\text{Dist}(B^*)$.

Test C: Bayesian Posterior p-Value

For each pair of training set and single test subject, a joint Bayesian hierarchical model (4) is fit. Based on the posterior distribution of $\delta$, one can compute the probability $p(\delta \leq 0 | Y\text{train}, Y\text{test}) = p(\beta\text{new} \geq \beta\text{pop} | Y\text{train}, Y\text{test})$. This probability can be interpreted as a p-value, under the Bayesian framework as the "support" of the hypothesis $\delta = 0$ under a one-sided alternative (when the support drops below 0.05, say, the supposition that $\delta$ is not positive is rejected). Across 300 copies of simulated datasets for each alternative (paired with test sets), the false negative rate of the posterior p-value based test can be estimated and averaged.

Test D: Wald Test for MLE Estimator $\hat{\delta}$

For each pair of training set and single test subject, the difference in scaling factor is estimated between the test subject and the population (as represented by the training data) using model equation 4, which yields the difference estimate $\hat{\delta}$. The R package nlme can be used to make this estimate. The nlme package also reports a Wald test statistic $\hat{\delta}/SE(\hat{\delta})$, and a p-value is calculated based on this test statistic assuming it has a t distribution under the null with a degree freedom based on the hierarchical linear model framework. The result of this test at level $\alpha$ is also summarized across 1000 pairs of simulated training set plus a single test subject to approximate the false positive and false negative rates.

ii. Results

Since in practice, the distribution of test subjects under the alternative is not known, the use of "gold standard" test subjects is an idealized evaluation, which is reported for Test B. The true error rates for Test B are not directly obtainable, but a closely related is evaluated, and more practical test referred to as B. For this test, the expected false negative rate will be calculated based on the overlapping area between the template distributions under the null and the an alternative constructed via a location shift of the null, which is obtainable. The model-based results Test C and Test D will also be assessed to understand the behavior of these tests in small samples.

Table 3 shows the simulated error rate under various hypothesized $\delta_0 = \beta_{pop} - \beta_{test}$ values using tests A-D. In the first row when $\delta_0 = 0$ (the first row), the test subjects are generated under the null hypothesis space, hence the corresponding quantities are False Positive Rates (FPR) of different tests. They are also the type I error rate. When $\delta_0 > 0$, the test subjects are generated under the alternative hypothesis space hence the remaining rows report the false negative rates (FNR or 1-power).

Focusing first on Test A for Scenario One when two weights are used, with a level 0.05 test, it can be seen that the FPR is 0.05 by construction (the critical value was based on the 5th percentile on the same distribution). FNRs are quite high at 46.1% even for a very strong alternative, as is given by the last entry ($\delta_0 = 1.3$). This is to be expected with a small test sample and a low FPR. Continuing to observe Test A, it can be seen that under Scenario Two to the right when three weights are used, the False Negative Rate decreases substantially. At $\delta = 0.7$, when the scaling factor of the test subject is half of that of the expected value of normal training subjects, the FNR is 39.1%. At greater $\delta$ values, the extra weight condition makes a big difference in terms of reducing the false negative rate and increasing the potential power of this test.

In comparison, the error rates of our proposed method Test B, using only the training data and the test design, are only slightly higher than those of Test A when the true sampling distribution of the scaling factor $\beta\text{new}$ is assumed to be known. In particular, the false positive of Test B is 5.6% suggesting that our proposed test is capable of controlling the type I error at the desired level.

Since in practice the expected error rates of Test B are unknown, under column Test B*, error rates are approximated by calculating the overlapping area of the null template distribution and the alternative template distribution when $\delta = \delta_0$ (derived using the method in for deriving template distribution described above, step 4). Both tests B and B*yield strikingly similar FPRs and FNRs under our range of scenarios, and these are also quite close to what the standard in Test A would expect. In addition, the standard error of Test B's and Be's FNRs can be estimated, which are found to range from 0.02 to 0.06 in nearly every instance, with smaller s.e. for Scenario Two. The availability of these standard errors allows us to report, in a practical setting, an estimated error rate with confidence interval for Test B using those quantities calculated under Test B*.

are evaluated empirically based on the posterior distribution of $\delta$, it is free from the small sample "curse." Indeed, the fully Bayesian hierarchical model performs a little better than Test A with respect to FNR under scenario one, which is when the information collected around test subject is more limited. This suggests that, if modelled under the correct data generating process, by jointly modeling the training data (under a stronger design) and the test subject, a slightly higher powered test can be attained.

TABLE 2

The comparison of error rates for different tests. The first column shows the true values of $\delta_0$ under which test data were generated. Two desired levels of test are considered, 5% and 10%. The first row shows the false positive rate of different tests. The remaining rows show the false negative rate since $\delta_0 > 0$. Since Test B is to be used in the clinical setting, the expected false negative rate associated with a given level of the test are shown in column "Test B*".

| | Scenario One | | | | | Scenario Two | | | | |
|---|---|---|---|---|---|---|---|---|---|---|
| $\delta_0$ | Test A | Test B | Test B* | Test C | Test D | Test A | Test B | Test B* | Test C | Test D |
| Level of Test: 5% | | | | | | | | | | |
| 0.0 | 0.050 | 0.056 | 0.050 | 0.053 | 0.250 | 0.050 | 0.043 | 0.050 | 0.043 | 0.326 |
| 0.1 | 0.934 | 0.936 | 0.935 | 0.916 | 0.660 | 0.895 | 0.922 | 0.917 | 0.933 | 0.623 |
| 0.2 | 0.915 | 0.928 | 0.916 | 0.900 | 0.609 | 0.835 | 0.868 | 0.870 | 0.876 | 0.552 |
| 0.3 | 0.893 | 0.882 | 0.895 | 0.870 | 0.597 | 0.777 | 0.785 | 0.807 | 0.806 | 0.467 |
| 0.4 | 0.859 | 0.871 | 0.869 | 0.846 | 0.535 | 0.673 | 0.722 | 0.729 | 0.690 | 0.451 |
| 0.5 | 0.828 | 0.841 | 0.839 | 0.813 | 0.486 | 0.592 | 0.633 | 0.637 | 0.593 | 0.360 |
| 0.6 | 0.792 | 0.820 | 0.804 | 0.800 | 0.431 | 0.488 | 0.530 | 0.537 | 0.510 | 0.256 |
| 0.7 | 0.754 | 0.763 | 0.766 | 0.750 | 0.357 | 0.391 | 0.421 | 0.435 | 0.400 | 0.224 |
| 0.8 | 0.715 | 0.732 | 0.724 | 0.660 | 0.343 | 0.287 | 0.338 | 0.337 | 0.293 | 0.179 |
| 0.9 | 0.668 | 0.666 | 0.678 | 0.590 | 0.316 | 0.202 | 0.246 | 0.250 | 0.206 | 0.136 |
| 1.0 | 0.618 | 0.633 | 0.630 | 0.536 | 0.251 | 0.133 | 0.160 | 0.177 | 0.110 | 0.086 |
| 1.1 | 0.581 | 0.592 | 0.579 | 0.480 | 0.219 | 0.080 | 0.112 | 0.119 | 0.073 | 0.072 |
| 1.2 | 0.516 | 0.546 | 0.527 | 0.416 | 0.193 | 0.052 | 0.069 | 0.077 | 0.043 | 0.044 |
| 1.3 | 0.461 | 0.455 | 0.475 | 0.380 | 0.156 | 0.029 | 0.044 | 0.047 | 0.020 | 0.042 |
| Level of Test: 10% | | | | | | | | | | |
| 0.0 | 0.100 | 0.103 | 0.100 | 0.110 | 0.307 | 0.100 | 0.086 | 0.100 | 0.073 | 0.366 |
| 0.1 | 0.879 | 0.868 | 0.875 | 0.866 | 0.614 | 0.824 | 0.848 | 0.846 | 0.863 | 0.566 |
| 0.2 | 0.852 | 0.851 | 0.846 | 0.836 | 0.562 | 0.739 | 0.772 | 0.777 | 0.766 | 0.513 |
| 0.3 | 0.818 | 0.797 | 0.812 | 0.810 | 0.527 | 0.669 | 0.663 | 0.692 | 0.670 | 0.437 |
| 0.4 | 0.768 | 0.769 | 0.775 | 0.790 | 0.478 | 0.551 | 0.595 | 0.596 | 0.580 | 0.403 |
| 0.5 | 0.726 | 0.739 | 0.734 | 0.740 | 0.441 | 0.467 | 0.496 | 0.494 | 0.483 | 0.314 |
| 0.6 | 0.681 | 0.696 | 0.689 | 0.660 | 0.379 | 0.355 | 0.390 | 0.393 | 0.370 | 0.218 |
| 0.7 | 0.629 | 0.638 | 0.641 | 0.583 | 0.304 | 0.273 | 0.297 | 0.298 | 0.260 | 0.184 |
| 0.8 | 0.595 | 0.600 | 0.590 | 0.526 | 0.296 | 0.183 | 0.211 | 0.216 | 0.170 | 0.147 |
| 0.9 | 0.539 | 0.528 | 0.539 | 0.453 | 0.273 | 0.124 | 0.141 | 0.150 | 0.103 | 0.111 |
| 1.0 | 0.485 | 0.481 | 0.486 | 0.406 | 0.218 | 0.079 | 0.082 | 0.099 | 0.066 | 0.073 |
| 1.1 | 0.445 | 0.450 | 0.434 | 0.340 | 0.179 | 0.042 | 0.060 | 0.062 | 0.036 | 0.058 |
| 1.2 | 0.381 | 0.400 | 0.384 | 0.280 | 0.153 | 0.027 | 0.030 | 0.037 | 0.020 | 0.036 |
| 1.3 | 0.328 | 0.334 | 0.335 | 0.240 | 0.124 | 0.013 | 0.021 | 0.021 | 0.013 | 0.033 |

With only one test subject, it is expected the power of the test will be low. However, when the level of the test is set to be 10%, the false negative rate is greatly reduced. When $\delta>0.7$, the False Negative Rate under Scenario Two for Test A is less than 20%, corresponding to a power of at least 80%, and the performance of Test B and Test B* continue to be very similar.

The performance of model-based tests C and D are also assessed in Table 2. Surprisingly, it find that Test D, the classical mixed effects model approach, fails to control the type I error rate at the proper level. For example, under scenario one, the false positive rate for Test D is 25% while the desired rate is 5%. This suggests that the Wald test relies strongly on asymptotic behavior and it is not appropriate for sample sizes associated with single-case design.

Figure 31B:
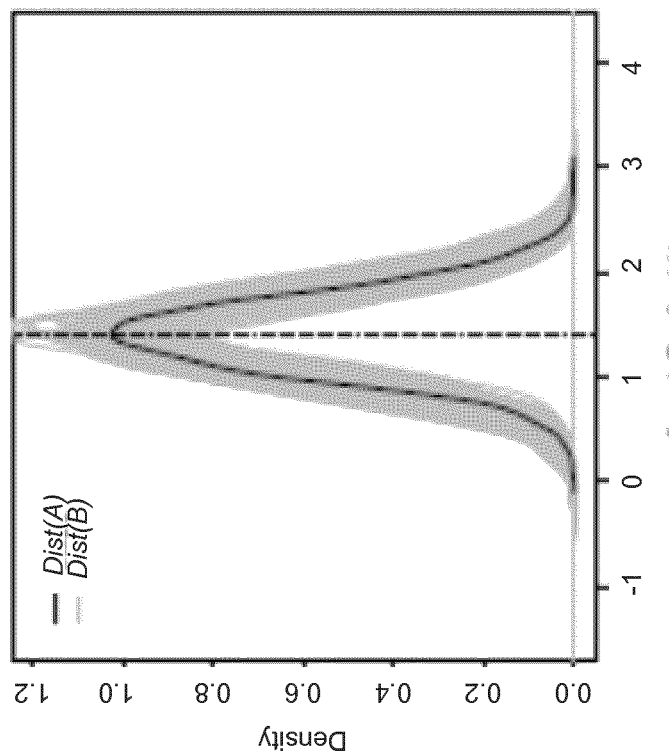
FIG. 31A and FIG. 31B Dist(A) is the true density of 0 under the null hypothesis. In grey are 100 realizations of Dist(B) under the null based on the proposed method using a single copy of simulated training set as the basis for the realized density estimate.
Figure 31A:
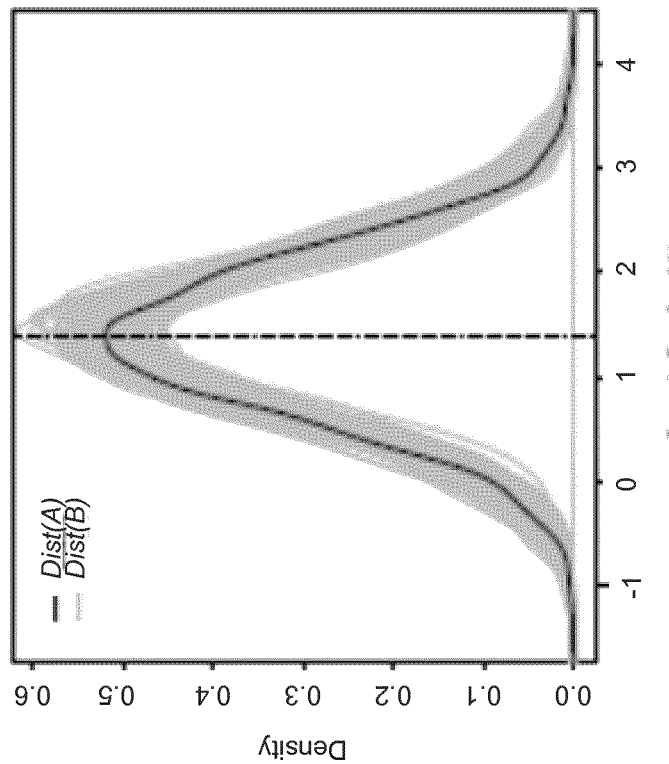

Test C, on the other hand, does a better job at controlling the FPR and manages to achieve FNRs that are comparable to the standard set by Test A. Since the p-values of Test C FIGS. 31A and 31B compare the sampling null distribution of $\bar\delta$ (Dist(A)) and the proposed alternative null distribution based on Bayesian posterior predictive draws (Dist (B)). Since multiple samples of Dist(B) are available, the variability inherent in model estimation can be displayed by superimposing 100 samples of this distribution upon the standard Dist(A). The left panel plots the results based on the two-weight design, and the right panel plots the results based on the three-weight design. As can be seen, the two distributions are fairly close, and the variability in Dist(B) is surprisingly small, considering that it is estimated from only 10 normal subjects. This is because the training data uses a stronger within-subject design where each subject lifts 10 different weights with more repeats.

What is claimed:
1. A computer-implemented machine for training or rehabilitating, comprising:

a base having one or more load force sensors for receiving force from one or more grasping objects;
a glove having two or more grip force sensors;
a processor; and
a tangible computer-readable medium operatively connected to the processor and including computer code configured to:
receive information from the one or more load force sensors and the two or more grip force sensors; and
determine a change in load force and determine a grip force exerted through the glove,
wherein the base further comprises a coaster configured to receive the one or more grasping objects.

2. The computer implemented machine of claim 1, wherein the computer code is further configured to determine if the change in load force and the group force are each within an identified range of acceptable states and if not, send information to a feedback mechanism to provide corrective feedback.

3. The computer-implemented machine for training or rehabilitating of claim 1, further wherein the coaster comprises a first leg, a second leg, and a third leg, and wherein the one or more load force sensors comprise a first load force sensor associated with the first leg, a second load force sensor associated with the second leg, and a third load force sensor associated with the third leg.

4. The computer-implemented machine for training or rehabilitating of claim 1, further comprising a capacitive sensor associated with the base and configured to start the computer-implemented machine.

5. The computer-implemented machine for training or rehabilitating of claim 1, further comprising computer code configured to receive an initial load information from the one or more load force sensors and determining a weight of the one or more objects associated with the base.

* * * * *

UNITED STATES PATENT AND TRADEMARK OFFICE
CERTIFICATE OF CORRECTION

PATENT NO. : 10,299,738 B2
APPLICATION NO. : 14/942971
DATED : May 28, 2019
INVENTOR(S) : Preeti Raghavan and Vikram Kapila Page 1 of 1

It is certified that error appears in the above-identified patent and that said Letters Patent is hereby corrected as shown below:

In the Specification

Column 1, following after the "Cross Reference to Related Applications" sub-heading and paragraph, add new sub-heading and paragraph:
STATEMENT OF GOVERNMENT INTEREST
"This invention was made with government support under K23 HD049472 awarded by the National Institutes of Health. The government has certain rights in the invention."

Signed and Sealed this
Twenty-sixth Day of August, 2025

Coke Morgan Stewart
*Acting Director of the United States Patent and Trademark Office*